(12) United States Patent
Sperl et al.

(10) Patent No.: US 6,420,410 B1
(45) Date of Patent: Jul. 16, 2002

(54) METHOD FOR TREATING NEOPLASIA BY EXPOSURE TO N,N'-SUBSTITUTED BENZIMIDAZOL-2-ONES

(75) Inventors: Gerhard Sperl, North Wales, PA (US); Ulrich Ixkes, Law (GB); Rifat Pamukcu, Spring House; Gary A. Piazza, Doylestown, both of PA (US)

(73) Assignee: Cell Pathways, Inc., Horsham, PA (US)

( * ) Notice: Subject to any disclaimer, the term of this patent is extended or adjusted under 35 U.S.C. 154(b) by 0 days.

(21) Appl. No.: 09/639,909

(22) Filed: Aug. 16, 2000

Related U.S. Application Data

(63) Continuation of application No. 09/200,138, filed on Nov. 24, 1998, now abandoned.

(51) Int. Cl.$^7$ ............................................. A61K 31/415
(52) U.S. Cl. ...................... 514/395; 514/391; 514/394
(58) Field of Search ................. 514/391, 394, 514/395

(56) References Cited

FOREIGN PATENT DOCUMENTS

WO     WO 95/19978     7/1995

*Primary Examiner*—Dwayne C. Jones
(74) *Attorney, Agent, or Firm*—Robert W. Stevenson

(57) ABSTRACT

A method for inhibiting neoplastic cells and related conditions by exposing them to N,N'-substituted benzimidazol-2-ones.

7 Claims, No Drawings

METHOD FOR TREATING NEOPLASIA BY EXPOSURE TO N,N'-SUBSTITUTED BENZIMIDAZOL-2-ONES

This application is a Continuation of prior U.S. application Ser. No. 09/200,138 filed on Nov. 24, 1998 entitled "Method For Treating Neoplasia by Exposure to N,N'-Substituted Benzimidazol-2-Ones," now abandoned, which is incorporated herein by reference.

TECHNICAL FIELD

This invention relates to compounds and methods for inducing or promoting apoptosis and for arresting uncontrolled neoplastic cell proliferation, methods that are specifically useful in the arresting and treatment of neoplasias, including precancerous and cancerous lesions.

BACKGROUND OF THE INVENTION

Pharmaceuticals that are effective against early stage neoplasias comprise an emerging and expanding area of research and potential commercial development. Such pharmaceuticals can delay or arrest development of precancerous lesions into cancers. Each year in the United States alone, untold numbers of people develop precancerous lesions, which exhibit a strong statistically significant tendency to develop into malignant tumors, or cancer. Such lesions include lesions of the breast (that can develop into breast cancer), lesions of the skin (that can develop into malignant melanoma or basal cell carcinoma), colonic adenomatous polyps (that can develop into colon cancer), cervical displasia (cervical cancer) and other such neoplasms.

Such compounds and methods are particularly beneficial to sub-populations of patients who repeatedly develop precancerous lesions, and therefore have a statistically higher probability of getting cancer. Many cancer types (e.g., breast, colon, prostate etc.) have such patient sub-populations.

The search for drugs useful for treating and preventing neoplasias in their earliest stages is intensive because chemotherapy and surgery on cancer itself is often not effective, and current cancer chemotherapy has severe side effects. Such cancer-preventative compounds are also envisaged for recovered cancer patients who retain a risk of cancer reoccurrence, and even for cancer patients who would benefit from compounds that selectively induce apoptosis in neoplastic, but substantially not in normal cells.

Because it is believed that chronic administration of cancer-preventative pharmaceuticals is necessary to inhibit or arrest the development of neoplasia, standard cancer chemotherapeutic drugs are not considered appropriate drugs for cancer chemoprevention because whatever cancer preventative (as opposed to cancer-fighting) capabilities those drugs may possess do not outweigh their severe side effects. Most standard chemotherapeutics are now believed to kill cancer cells by inducing apoptosis (also sometimes referred to as "programmed cell death"). Apoptosis naturally occurs in many tissues in the body. Apoptosis plays a critical role in tissue homeostasis, that is, it ensures that the number of new cells produced are correspondingly offset by an equal number of cells that die. Apoptosis is especially pronounced in self-renewing tissues such as bone marrow, immune cells, gut, and skin. For example, the cells in the intestinal lining divide so rapidly that the body must eliminate cells after only three days to protect and prevent the overgrowth of the intestinal lining.

Standard chemotherapeutics promote apoptosis not only in cancer cells, but also in normal human tissues, and therefore have a particularly severe effect on tissues where apoptosis is especially pronounced (e.g. hair, gut and skin). The results of those effects include hair loss, weight loss, vomiting and bone marrow immune suppression. Thus, standard chemotherapeutics are inappropriate for cancer prevention, particularly if chronic administration is indicated.

Several non-steroidal anti-inflammatory drugs ("NSAIDs"), originally developed to treat arthritis, have shown effectiveness in inhibiting and eliminating colonic polyps. Polyps virtually disappear when the patients take the drug, particularly when the NSAID sulindac is administered. However, the continued prophylactic use of currently available NSAIDs, even in high colon cancer-risk patients, is still marked by severe side reactions that include gastrointestinal irritations, perforations, ulcerations and kidney toxicity believed to be produced by inhibition of prostaglandin synthetase activity ("PGE-2"). Such inhibition is a requirement for the NSAIDs anti-inflammatory action since elevated levels of PGE-2 are associated with inflammation. PGE-2 plays a protective function in the gastrointestinal tract, which is the reason such gastric side effects arise with chronic NSAID therapy, which is rarely indicated for arthritis sufferers, acute therapy being the norm for them. However, chronic administration of sulindac is important for high cancer-risk patients to eliminate and prevent future polyps which causes gastric side effects in many such patients. Once NSAID treatment is terminated due to such complications, the neoplasms return, particularly in high risk patients.

Compounds such as those disclosed in U.S. Pat. No. 5,643,959 have exhibited advantages in the treatment of neoplastic lesions since such compounds have been shown to induce apoptosis in neoplastic cells but not in normal cells in humans. Thus, the severe side effects due to induction of apoptosis in normal cells by conventional chemotherapeutics are avoided by these novel therapeutics (see, Van Stock, et al., *Gastroenterology*, 112 (4): A673, 1997). In addition, such compounds do not exhibit the gastric side effects associated with NSAIDs since such compounds do not substantially inhibit PGE-2. More potent compounds with such neoplasia specificity but without substantial PGE-2 activity are desirable.

SUMMARY OF THE INVENTION

This invention represents potent compounds that induce apoptosis in neoplastic cells (but not substantially in normal cells), for treating patients with neoplastic lesions without substantially inhibiting PGE-2. This invention also involves methods for inducing such specific apoptosis in neoplastic cells by exposing such cells to a pharmacologically effective amount of those compounds described below to a patient in need of such treatment. Such compositions are effective in modulating apoptosis and modulating the growth of neoplasms, but are not suffering from the side effects of conventional chemotherapeutics and NSAIDs.

DETAILED DESCRIPTION OF THE INVENTION

As discussed above, the present invention includes compounds of Formula I below

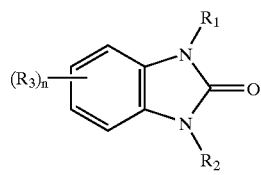

wherein $R_1$ is selected from a group consisting of lower alkyl, $-(CR_6R_7)-(CH_2)_x-C(O)-OR_4$, $-(CH_2)_x-C(O)NHR_5$, or $-(CH_2)_x-C(O)-NR_6R_7$;

$R_2$ is selected from a group consisting of lower alkyl, alkenyl, $-(CH_2)_m-R_8$, substituted or unsubstituted aryl wherein said aryl group is selected from the group consisting of phenyl, benzyl, pyridyl, pyrimidyl, pyrazinyl, piperidyl, imidazolyl, indolyl, triazinyl, tetrazolyl, thiophenyl, furanyl, thiazolyl, pyrazolyl, and pyrrolyl, and wherein said substituents are one to five selected from the group consisting of halogen, lower alkyl, lower alkoxy, amino, nitro, and alkoxycarbonyl;

$R_3$ is selected from a group consisting of halogen, lower alkoxy, lower alkyl, benzoyl, nitro, haloalkyl, alkoxycarbonyl, lower alkenoxy, and aryloxy, wherein said aryl group is selected from a group consisting of phenyl and benzyl;

$R_4$ is hydrogen or lower akyl;

$R_5$ is selected from a group consisting of hydrogen, lower alkyl, benzyl, pyridyl, pyrimidinyl, pyrazinyl, imidazolyl, indolyl, triazinyl, tetrazolyl, thiophenyl, furanyl, thiazolyl, pyrazolyl, and pyrrolyl;

$R_6$ and $R_7$ are independently selected from a group consisting of hydrogen, lower alkyl, tetrahydrofuranyl, tetrahydrofuranyl methyl, $-(CH_2)_x-C(O)-NH_2$, $-(CH_2)_x-C(O)-OR_4$, lower alkoxy, cyclohexylmethyl, substituted or unsubstituted phenyl, piperidyl, and benzyl, wherein said substituents are one to three selected from the group consisting of halogen, lower alkyl, lower alkoxy, lower alkoxycarbonyl, and diethylamine;

$R_8$ is selected from a group consisting of CN, alkylcarbonyloxy, lower alkylcarbonyl, and arylcarbonyloxy, wherein said aryl is one from a group consisting of phenyl and benzyl;

x is 0, 1 or 2;

m is 0, 1, 2 or 3; and n is 0, 1, or 2.

Preferred compounds of Formula I include those wherein $R_1$ is selected from a group consisting of lower alkyl, $-(CH_2)_x-C(O)-NHR_5$, or $-(CH_2)_x-C(O)-NR_6R_7$;

$R_2$ is selected from a group consisting of substituted or unsubstituted aryl wherein said aryl group is selected from the group consisting of phenyl, benzyl, pyridyl, pyrimidyl, triazinyl, tetrazolyl, thiophenyl, furanyl, thiazolyl, pyrazolyl, and pyrrolyl, and wherein said substituents are one to three selected from the group consisting of halogen, lower alkoxy, amino, nitro, and alkoxycarbonyl;

$R_3$ is selected from a group consisting of halogen, lower alkoxy, lower alkyl, benzoyl, nitro, haloalkyl, alkoxycarbonyl, and aryloxy, wherein said aryl group is selected from a group consisting of phenyl and benzyl;

$R_5$ is selected from a group consisting of benzyl, pyridyl, pyrimidinyl, triazinyl, tetrazolyl, thiophenyl, furanyl, pyrazolyl, and pyrrolyl;

$R_6$ and $R_7$ are independently selected from a group consisting $-(CH_2)_x-C(O)-NH_2$, cyclohexylmethyl, substituted phenyl and benzyl, wherein said substituents are one or two selected from the group consisting of halogen, lower alkoxy, lower alkoxycarbonyl, and diethylamine;

$R_8$ is selected from a group consisting of lower alkylcarbonyl, and arylcarbonyloxy, wherein said aryl is benzyl;

x is 0, 1 or 2;

m is 0, 1, or 2; and n is 0, 1, or 2.

The most preferred group of compounds of this invention include those more preferred compounds of Formula I wherein $R_1$ is selected from a group consisting of $-(CH_2)_x-C(O)-NHR_5$, or $-(CH_2)_x-C(O)-NR_6R_7$;

$R_2$ is selected from a group consisting of substituted aryl wherein said aryl group is selected from the group consisting of phenyl, benzyl, pyridyl, pyrimidyl, and triazinyl, and wherein said substituents are two or three selected from the group consisting of halogen, lower alkoxy, amino, nitro, and alkoxycarbonyl;

$R_3$ is selected from a group consisting of halogen, lower alkoxy, benzoyl, haloalkyl, and alkoxycarbonyl, wherein said aryl group is selected from a group consisting of phenyl and benzyl;

$R_4$ is lower alkyl;

$R_5$ is selected from a group consisting of benzyl, pyridyl, pyrimidinyl, and triazinyl, $R_6$ and $R_7$ are independently selected from a group consisting $-(CH_2)_x-C(O)-NH_2$, substituted phenyl and benzyl, wherein said substituents are two selected from the group consisting of lower alkoxy, and diethylamine;

$R_8$ is arylcarbonyloxy, wherein said aryl is benzyl;

x is 0 or 1;

m is 0 or 1; and n is 0 or 1.

The present invention is also a method of treating individuals with neoplastic lesions by administering a pharmacologically effective amount of an enterically coated pharmaceutical composition that includes compounds of this invention.

Preferably, such compounds are administered without therapeutic amounts of an NSAID.

Also, the present invention is a method of inhibiting the growth of neoplastic cells by exposing the cells to an effective amount of compounds of Formula I, wherein $R_1$, $R_2$, $R_3$, $R_4$, $R_5$, $R_6$, $R_7$, $R_8$, m, n, and x are defined as above.

In still another form, the invention is a method of inducing apoptosis in human cells by exposing those cells to an effective amount of compounds of Formula I, wherein $R_1$ through $R_8$ m, n, and x are defined as above where such cells are sensitive to these compounds.

Additionally, in yet another form, the invention is a method of treating a patient having a disease which would benefit from regulation of apoptosis by treating the patient with an effective amount of compounds of Formula I, wherein $R_1$ through $R_8$ etc. are defined as above. The regulation of apoptosis is believed to play an important role in diseases associated with abnormalities of cellular growth patterns such as benign prostatic hyperplasia, neurodegenerative diseases such as Parkinson's disease, autoimmune diseases including multiple sclerosis and rheumatoid arthritis, infectious diseases such as AIDS, and other diseases, as well.

As used herein, the term "precancerous lesion" includes syndromes represented by abnormal neoplastic, including dysplastic, changes of tissue. Examples include dysplasic growths in colonic, breast, bladder or lung tissues, or conditions such as dysplastic nevus syndrome, a precursor to malignant melanoma of the skin. Examples also include, in addition to dysplastic nevus syndromes, polyposis syndromes, colonic polyps, precancerous lesions of the cervix (i.e., cervical dysplasia), esophagus, prostatic dysplasia, bronchial dysplasia, breast, bladder and/or skin and related conditions (e.g., actinic keratosis), whether the lesions are clinically identifiable or not.

As used herein, the term "cancerous" refers to lesions that are malignant. Examples include malignant melanomas, breast cancer, prostate cancer and colon cancer.

As used herein, the term "neoplasm" refers to both precancerous and cancerous lesions and hyperplasia.

As used herein, the term "halo" or "halogen" refers to chloro, bromo, fluoro and iodo groups, and the term "alkyl" refers to straight, branched or cyclic alkyl groups and to administration are most preferred. substituted aryl alkyl groups. The term "lower alkyl" refers to $C_1$ to $C_8$ alkyl groups.

The term "lower alkoxy" refers to alkoxy groups having from 1 to 8 carbons, including straight, branched or cyclic arrangements.

The term "pharmaceutically acceptable salt" refers to non-toxic acid addition salts and alkaline earth metal salts of the compounds of Formula I. The salts can be prepared in situ during the final isolation and purification of such compounds, or separately by reacting the free base or acid functions with a suitable organic acid or base, for example. Representative acid addition salts include the hydrochloride, hydrobromide, sulfate, bisulfate, acetate, valerate, oleate, palmatate, stearate, laurate, borate, benzoate, lactate, phosphate, tosylate, mesylate, citrate, maleate, fumarate, succinate, tartrate, glucoheptonate, lactobionate, lauryl sulfate salts and the like. Representative alkali and alkaline earth metal salts include the sodium, calcium, potassium and magnesium salts.

Compounds of this invention may be formulated into pharmaceutical compositions together with pharmaceutically acceptable carriers for oral administration in solid or liquid form, or for rectal or topical administration, although carriers for oral Pharmaceutically acceptable carriers for oral administration include capsules, tablets, pills, powders, troches and granules. In such solid dosage forms, the carrier can comprise at least one inert diluent such as sucrose, lactose or starch. Such carriers can also comprise, as is normal practice, additional substances other than diluents, e.g., lubricating agents such as magnesium stearate. In the case of capsules, tablets, troches and pills, the carriers may also comprise buffering agents. Carriers such as tablets, pills and granules can be prepared with enteric coatings on the surfaces of the tablets, pills or granules. Alternatively, the enterically coated compound can be pressed into a tablet, pill, or granule, and the tablet, pill or granules for administration to the patient. Preferred enteric coatings include those that dissolve or disintegrate at colonic pH such as shellac or Eudraget S.

Pharmaceutically acceptable carriers include liquid dosage forms for oral administration, e.g., pharmaceutically acceptable emulsions, solutions, suspensions, syrups and elixirs containing inert diluents commonly used in the art, such as water. Besides such inert diluents, compositions can also include adjuvants such as wetting agents, emulsifying and suspending agents, and sweetening, flavoring and perfuming agents.

Pharmaceutically acceptable carriers for topical administration include DMSO, alcohol or propylene glycol and the like that can be employed with patches or other liquid-retaining material to hold the medicament in place on the skin so that the medicament will not dry out.

Pharmaceutically acceptable carriers for rectal administration are preferably suppositories that may contain, in addition to the compounds of this invention excipients such as cocoa butter or a suppository wax, or gel.

The pharmaceutically acceptable carrier and compounds of this invention are formulated into unit dosage forms for administration to a patient. The dosage levels of active ingredient (i.e., compounds of this invention) in the unit dosage may be varied so as to obtain an amount of active ingredient effective to achieve lesion-eliminating activity in accordance with the desired method of administration (i.e., oral or rectal). The selected dosage level therefore depends upon the nature of the active compound administered, the route of administration, the desired duration of treatment, and other factors. If desired, the unit dosage may be such that the daily requirement for active compound is in one dose, or divided among multiple doses for administration, e.g., two to four times per day.

The pharmaceutical compositions of this invention are preferably packaged in a container (e.g., a box or bottle, or both) with suitable printed material (e.g., a package insert) containing indications, directions for use, etc.

There are several general schemes for producing compounds useful in this invention.

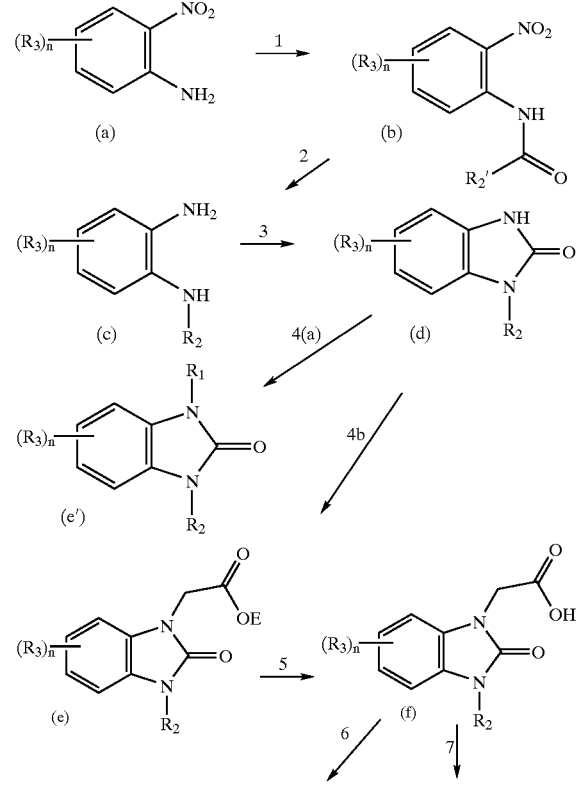

Scheme I

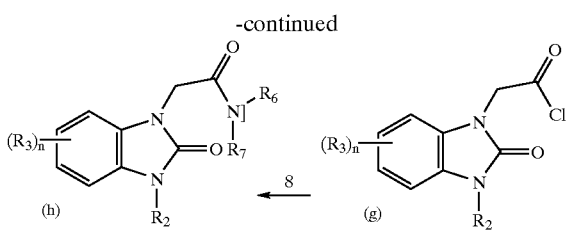

The substituted 2-nitro-aniline (a) in dichloromethane is charged in the presence of pyridine with the acid chloride $R_2'$—C(O)—Cl (reaction 1). The resulting nitro-substituted amide (b) is reduced with LiAlH$_4$ in ether (reaction 2). Reaction with triphosgene in dichloromethane performs the ring closure to the benzimidazol-2-one (d) (reaction 3). The substitution with $R_1$ is performed with sodium hydride in dimethylacetamide and the halogenide $R_1$-Hal (reaction 4) to yield the ester (e) (where OE=alkoxy)or the compound (e'). The ester (e) can be saponified to the acid (f) with potassium hydroxide in ethanol (reaction 5). Reaction of the acid (f) with 1-(3-dimethylaminopropyl)-3-ethyl-carbodiimide HCl and the amine HNR$_6$R$_7$ gives the corresponding amide (h) (reaction 6). Alternatively, the acid (f) can be transformed into the acid chloride (g) by reaction with thionyl chloride (reaction 7). The acid chloride (g) is then allowed to react with an amine HNR$_6$R$_7$ to the corresponding amide (h).

Another method of obtaining the benzimidazol-2-one (d) is described in the following scheme II.

Scheme II

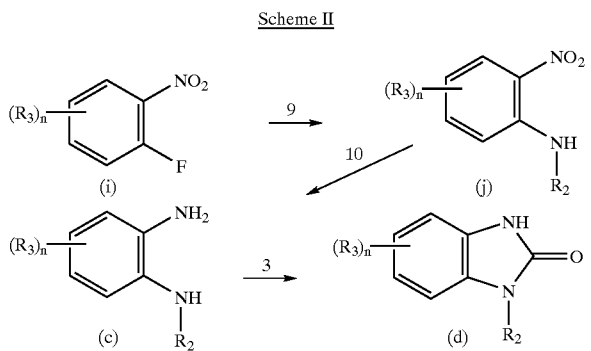

Starting with the substituted 2-fluoro-nitrobenzene (i), the nitroaniline (j) is obtained by the reaction 9 with amine $R_2$—NH$_2$. The nitroaniline (j) is reduced with SnCl$_2$2H$_2$O in ethyl acetate under reflux to the corresponding amine (c) (reaction 10), which is further allowed to react with triphosgene in order to yield the benzimidazol-2-one (d) (reaction 3).

The foregoing may be better understood from the following examples that are presented for the purposes of illustration and are not intended to limit the scope of the invention. As used in the following examples, the references to substituents such as $R_1$, $R_2$, etc. refer to the corresponding substituents in Formula I above.

EXAMPLES

Example 1

Ethyl 2-[2-Oxo-3-benzylenzimidazolyl]acetate (A.) [N-(2-nitrophenyl)]-benzylamine Benzylamine (0.12 mol, 13.0 ml) in chloroform (70 ml) is charged slowly with 2-fluoronitrobenzene (0.06 mol, 6.32 ml) in chloroform (50 ml); the mixture is stirred at room temperature for 17 hours and is refluxed for 4 hours. The reaction mixture is added dropwise into water (100 ml) and extracted with chloroform (3×30 ml). The combined organic layers are dried with MgSO$_4$, filtered and the solvent evaporated. Recrystallisation from ethanol yields the title product as an orange solid (11.5 g).

(B.) [N-(2-Aminophenyl)]-benzylamine

[N-(2-Nitrophenyl)]-benzylamine (21.9 mmol, 5.0 g) in ethyl acetate (150 ml) is charged with SnCl$_2$2H$_2$O (131 mmol, 29.55 g) and is refluxed for 3 hours. The mixture is poured into ice water (100 g), sodium bicarbonate is added to achieve pH 7, and the reaction mixture is extracted with ethyl acetate (3×50 ml). The organic layer is dried with MgSO$_4$, is filtered and evaporated to yield a light sensitive oil, which is used as such in the next step.

(C.) 1-Benzyl-3-hydrobenzimidazol-2-one

[N-(2-Aminophenyl)]-benzylamine (15.1 mmol, 3.0 g) in dichloromethane (80 ml) is charged with triphosgene (5.3 mmol, 1.57 g) in dichloromethane (40 ml) and is stirred at room temperature over the weekend. The suspension is poured into water (100 g) and is extracted with dichloromethane (2×50 ml). The organic layer is a suspension The colorless solid is filtered off, is dried in vacuo and is recrystallized from ethyl acetate to give the title product (81%)($R_1$=H, $R_2$=benzyl, n=0).

(D) Ethyl 2-[2-Oxo-3-benzylenzimidazolyl]acetate

Sodium hydride (14.1 mmol, 0.56 g, 60% mineral oil) is dissolved in dimethylacetamide (10 ml). 1-Benzyl-3-hydrobenzimidazol-2-one (9.1 mmol, 2.0 g) (example 1) in dimethylacetamide (10 ml) is added dropwise to the ice cooled solution which is stirred for 1 hour. Ehtylbromoacetate (14.1 mmol, 1.57 ml) in dimethylacetamide (5 ml) is added, and the mixture is stirred 24 hours at room temperature. The solution is added dropwise into ice (300 g) and the precipitate is filtered off, added to a 1:1 dichloromethane/water mixture and is extracted with dichloromethane (3×20 ml). The combined organic layers are dried with MgSO$_4$, filtered and evaporated. Recrystallisation from ethyl acetate yields the title compound as a colorless solid (64%)($R_1$=CH$_2$—C(O)—OEt, $R_2$=benzyl, n=0).

Example 3

2-(2-Oxo-3-benzylbenzimidazolyl) Acetic Acid

Ethyl 2-(2-oxo-3-benzylbenzimidazolyl)acetate (4.19 mmol, 1.3 g) (example 1) is added to potassium hydroxide (13.41 mmol, 0.75 g) in ethanol (10 ml), and the mixture is stirred at reflux for 2 hours. The solvent is evaporated and water (40 ml) is added. The pH is adjusted to 1–2 with concentrated hydrochloric acid. The colorless precipitate is filtered off and dried in vacuo to yield the title compound (87%) ($R_1$=CH$_2$—C(O)—OH, $R_2$=benzyl, n=0).

Example 3

2(2-Oxo-3-benzylbenzimidazolyl)-N-benzylethanamide 2-(2-oxo-3-benzylbenzimidazolyl)acetic acid (1.77 mmol, 0.5 g) (example 2) in DMA (5 ml) is charged with 1-(3-dimethylaminopropyl)-3-ethyl-carbodiimide HCl (2.66 mmol, 0.51 g). Benzylamine (2.48 mmol, 0.27 ml) is added to the suspension, and the mixture is stirred at room temperature for 17 hours. The solution is added dropwise into ice (50 g) and the colorless precipitate is filtered off and dried in vacuo. Recrystallisation from ethyl acetate yields the title product (47%) ($R_1$=CH$_2$—C(O)—NHR$_5$, $R_5$=benzyl, $R_2$=benzyl, n=0).

Example 4

Ethyl-2-[6-fluoro-2-oxo-3-(3,4,5-trimethoxybenzyl-)-3-Hydrobenzimidazolyl]acetate (A.) [N-(4-Fluoro-2-nitrophenyl)]3,4,5-trimethoxybenzylamide 4-Fluoro-2-nitroaniline (20 mmol, 3.1 g) in dichloromethane (50 ml) and pyridine (30 mmol, 2.4 ml) is stirred with 3,4,5-trimethoxybenzoylchloride (30 mmol, 6.9 g) in dichloromethane (30 ml) for 2 days at room temperature. The title compound precipitates out of solution in the freezer, is filtered and dried in vacuo to give the title compound as a yellowish solid (66%).

(B.) [N-(2-amino-4-fluorophenyl)]-3,4,5-trimethoxybenzylamine

N-(4-Fluoro-2-nitrophenyl) 3,4,5-trimethoxybenzylamide (17.1 mmol, 6.0 g) in absolute ether (100 ml) is added to $LiAlH_4$ (63.4 mmol, 2.4 g) in absolute ether (40 ml) and the mixture is stirred at room temperature for 16 hours. While cooling with an ice bath, the suspension is quenched with water (40 ml) and is extracted with ether (3×100 ml). The combined organic layers are dried with $MgSO_4$, filtered and evaporated. Flash-chromatography (hexane:ethylacetate 1:1) and subsequent recrystallisation from ethanol yield the title product.

(C.) 5-Fluoro-1-(3,4,5-trimethoxybenzyl-)3-hydrobenzimidazol-2-one (2-Amino-4-fluorophenyl)-3,4,5-trimethoxybenzylamine (10 mmol, 3.1 g) in dichloromethane (50 ml) is charged with triphosgene (3.5 mmol, 1.04 g) in dichloromethane (25 ml). The mixture is stirred at room temperature for 15 hours, is added to water (100 ml) and is extracted with dichloromethane (3×25 ml). The combined organic phases are dried with $MgSO_4$, filtered and evaporated. Digestion with ethyl acetate (40 ml) yields the title compound in the ethyl acetate phase, which is dried in vacuo, as an off-white solid ($R_1$=H, $R_2$=3,4,5-trimethoxybenzyl, $R_3$=F, n=1).

(D) Ethyl-2-[6-fluoro-2-oxo-3-(3,4,5-trimethoxybenzyl-)3-hydrobenzimidazolyl]acetate Sodium hydride (6.77 mmol, 0.27g, 60% in mineral oil) is dissolved in dimethylacetamide (10 ml). 5-Fluoro-1-(3,4,5-trimethoxybenzyl-)3-hydrobenzimidazol-2-one (4.5 mmol, 1.5 g) (example 4) in dimethylacetamide (10 ml) is added slowly, and the mixture is stirred at 0° C. for 1 hour. Ethylbromoacetate (6.77 mmol, 0.75 ml) is added, and the reaction mixture is allowed to stir at room temperature for 60 hours. The solution is added dropwise onto ice (300 g), and the precipitate is filtered off. Extraction with dichloromethane gives the title compound that is recrystallized from ethyl acetate to give as pink needles (64%) ($R_1$=$CH_2$—C(O)—OEt, $R_2$=3,4,5-trimethoxybenzyl, $R_3$=F, n=1).

Example 5

2-[6-Fluoro-2-oxo-3-(3,4,5-trimethoxybenzyl-)3-hydrobenzimidazolyl]acetic Acid Ethyl-2-[6-fluoro-2-oxo-3-(3,4,5-trimethoxybenzyl-)3-hydrobenzimidazolyl]acetate (2.4 mmol, 1.0 g) (example 4) is added to potassium hydroxide (7.85 mmol, 0.45 g) in ethanol (20 ml), and the mixture is stirred at reflux for 2 hours. The solvent is evaporated and water (10 ml) is added. The pH is adjusted to 1–2 with concentrated hydrochloric acid. The colorless precipitate is filtered off and dried in vacuo to yield the title compound (78%) ($R_1$=$CH_2$—C(O)—OH, $R_2$=3,4,5-trimethoxybenzyl, $R_3$=F, n=1).

Example 6

2-[6-Fluoro-2-oxo-3-(3,4,5-trimethoxybenzyl-)3-hydrobenzimidazolyl]N-benzyl-acetamide (A.) 2-[6-Fluoro-2-oxo-3-(3,4,5-trimethoxybenzyl-)3-hydrobenzimidazolyl]acetyl Chloride 2-[6-Fluoro-2-oxo-3-(3,4,5-trimethoxybenzyl-)3-hydrobenzimidazolyl]acetic acid (1.28 mmol, 0.5 g) (example 5) is charged with thionyl chloride (7.7 mmol, 0.56 ml) and dimethylformamide (0.03 ml), and the mixture is heated at reflux for 1 hour. The solution is cooled down and the excess thionyl chloride and the DMF are removed. The title compound, a brownish solid, is used in the next step as such.

(B.) 2-[6-Fluoro-2-oxo-3-(3,4,5-trimethoxybenzyl-)3-hydrobenzimidazolyl]N-benzyl-acetamide A mixture of benzylamine (1.83 mmol, 0.2 ml) and pyridine (1.65 mmol, 0.13 ml) in dichloromethane is charged with ethyl-2-[6-fluoro-2-oxo-3-(3,4,5-trimethoxybenzyl-)3-hydrobenzimidazolyl]acetyl chloride in dichloromethane (10 ml) and is stirred at room temperature for 6 hours. The reaction mixture is poured onto ice water (50 g) and dichloromethane (50 ml). The aqueous phase is extracted with dichloromethane (2×20 ml), the combined organic layers are dried with $MgSO_4$, filtered and evaporated. Purification by column chromatography yields the title compound, which is recrystallized in ethyl acetate ($R_1$=$CH_2$—C(O)—$NHR_5$, $R_5$=benzyl, $R_2$=3,4,5-trimethoxybenzyl, $R_3$=F, n=1).

Example 9

Ethyl 2-[6-Methoxy-2-oxo-3-(3,4,5-trimethoxybenzyl-)3-hydrobenzimidazolyl]acetate (A.) [N-(4-methoxy-2-nitrophenyl)]-3,4,5-trimethoxybenzylamide 4-Methoxy-2-nitroaniline (20 mmol, 3.1 g) in dichloromethane (50 ml) and pyridine (30 mmol, 2.4 ml) is stirred with 3,4,5-trimethoxybenzylchloride (30 mmol, 6.9 g) in dichloromethane (30 ml) over night at room temperature. The solution precipitates, is filtrated and dried in vacuo to give the title compound (86%).

(B.) (2-Amino-4-methoxyphenyl)-3,4,5-trimethoxybenzylamine

[N-(4-methoxy-2-nitrophenyl)]3,4,5-trimethoxybenzylamide (17.1 mmol, 6.0 g) in absolute ether (100 ml) is added to $LiAlH_4$ (63.4 mmol, 2.4 g) in absolute ether (40 ml), and the mixture is stirred at room temperature for 8–9 hours. While cooling with an ice bath, the suspension is quenched with water (40 ml) and is extracted with ether (3×100 ml). The combined organic layers are dried with $MgSO_4$, filtered and evaporated. Recrystallisation from ethanol yields the title product as a red solid (23%).

(C.) 5-Methoxy-1-(3,4,5-trimethoxybenzyl-)3-hydrobenzimidazol-2-one

[(2-Amino-4-methoxyphenyl)]-3,4,5-trimethoxybenzylamine (10 mmol, 3.1 g) in dichloromethane (50 ml) is charged with triphosgene (3.5 mmol, 1.04 g) in dichloromethane (25 ml). The mixture is stirred at room temperature for 15 hours, is added to water (100 ml) and is extracted with dichloromethane (3×25 ml). The combined organic phases are dried with $MgSO_4$, filtered and evaporated. Digestion with ethyl acetate (40 ml) yields the title compound.

(D) Ethyl 2-[6-Methoxy-2-oxo-3-(3,4,5-trimethoxybenzyl-)3-hydrobenzimidazolyl]acetate Sodium hydride (8.72 mmol, 0.35 g, 60% in mineral oil) is dissolved in dimethylacetamide (10 ml). 5-Methoxy-1-(3, 4,5-trimethoxybenzyl-)3-hydrobenzimidazol-2-one (5.8 mmol, 2.0 g) in dimethylacetamide (10 ml) is added at 0° C. slowly, and the mixture is stirred at 0° C. for 1 hour. Ethylbromoacetate (8.72 mmol, 0.97 ml) is added, and the reaction mixture is allowed to stir at room temperature for 24 hours. The solution is added dropwise onto ice (300 g), and the precipitate is filtered off. Extraction with dichloromethane gives the title compound as colorless crystals that are recrystallized in ethyl acetate (72%) ($R_1$=$CH_2$—C(O)—OEt, $R_2$=3,4,5-trimethoxybenzyl, $R_3$=$OCH_3$, n=1).

Example 11

2-[6-Methoxy-2-oxo-3-(3,4,5-trimethoxybenzyl-)3-hydrobenzimidazolyl]acetic Acid

2-[6-Methoxy-2-oxo-3-(3,4,5-trimethoxybenzyl-)3-hydrobenzimidazolyl]acetate (3.48 mmol, 1.5 g) (example 7) is added to potassium hydroxide (11.14 mmol, 0.62 g) in ethanol (20 ml), and the mixture is stirred at reflux for 2 hours. The solvent is evaporated and water (10 ml) is added. The pH is adjusted to 1–2 with concentrated hydrochloric acid. The colorless precipitate is filtered off and dried in vacuo to yield the title compound (94%)($R_1$=$CH_2$—C(O)—OH, $R_2$=3,4,5-trimethoxybenzyl, $R_3$=$OCH_3$, n=1).

Example 12

2-[6-Methoxy-2-oxo-3-(3,4,5-trimethoxybenzyl-)3-hydrobenzimidazolyl]N-benzylethanamide 2-[6-Methoxy-2-oxo-3-(3,4,5-trimethoxybenzyl-)3-hydrobenzimidazolyl]acetic acid (1.99 mmol, 0.8 g) (example 8) in DMA (5 ml) is charged with 1-(3-dimethylamino-propyl)-3-ethyl-carbodiimide HCl (2.99 mmol, 0.57 g). Benzylamine (2.74 mmol, 0.3 ml) is added to the suspension, and the mixture is stirred at room temperature for 17 hours. The solution is added dropwise into ice (50 g) and the colorless precipitate is filtered off and dried in vacuo. Recrystallisation from ethyl acetate yields the title product ($R_1$=$CH_2$—C(O)—$NHR_5$, $R_5$=benzyl, $R_2$=3,4,5-trimethoxybenzyl, $R_3$=$OCH_3$, n=1).

Example 10

Ethyl 2-(3-(3,4,5-Trimethoxybenzyl)-2-oxo-benzimidazolyl)acetate (A.) [(2-Nitrophenyl)]-3,4,5-trimethoxybenzylamine 3,4,5-Trimethoxybenzylamine (0.6 mol, 10.29 ml) is charged slowly with 1-fluoro-2-nitrobenzene (0.04 mol, 3.74 ml) in dichloromethane (40 ml); and the mixture is stirred at room temperature for 17 hours. It is poured into water (100 ml) and extracted with dichloromethane (3×20 ml). The combined organic layers are washed with saturated sodiumbicarbonate (3×15 ml) and with water, they are dried with $MgSO_4$, filtered and evaporated. Recrystallisation from ethyl acetate yields the title product as an orange solid (70%).

(B.) [(2-Aminophenyl)]-3,4,5-trimethoxybenzylamine

[(2-Nitrophenyl)]-3,4,5-trimethoxybenzylamine (15.01 mmol, 5.0 g) in ethyl acetate (150 ml) is charged with $SnCl_2 2H_2O$ (94.2 mmol, 7.84 ml), and is refluxed for four (4) hours. The mixture is poured into ice water (100 g), sodium bicarbonate is added to achieve pH 7. and the reaction mixture is extracted with ethyl acetate (3×50 ml). The organic layers are dried with $MgSO_4$, are filtered and evaporated (45%)

(C.) 1-(3,4,5-Trimethoxybenzyl)-3-hydrobenzimidazol-2-one

[(2-Aminophenyl)]-3,4,5-trimethoxybenzylamine (7.11 mmol, 2.05 g) in dichloromethane (50 ml) is charged with triphosgene (2.36 mmol, 0.7 g) in dichloromethane (20 ml) and is stirred at room temperature over night. The suspension is poured into water (100 g) and is extracted with dichloromethane (2×50 ml). The organic layer is a suspension which is filtered off. The colorless solid is dried in vacuo and is recrystallized from dichloromethane to give the title product (99%).

(D.) Ethyl 2-(3-(3,4,5-Trimethoxybenzyl)-2-oxo-benzimidazolyl)acetate

Sodium hydride (14.1 mmol, 0.56 g, 60% mineral oil) is dissolved in dimethylacetamide (10 ml) 1-(3,4,5-trimethoxybenzyl)-3-hydrobenzimidazol-2-one (9.1 mmol, 2.86 g) (example 13) in dimethylacetamide (10 ml) is added dropwise to the ice cooled solution which is stirred for 1 hour. Ethylbromoacetate (14.1 mmol, 1.57 ml) in dimethylacetamide (5 ml) is added, and the mixture is stirred 24 hours at room temperature. The solution is added dropwise into ice (300 g), and the precipitate is filtered off. The solid is added to a 1:1 dichloromethane/water mixture and is extracted with dichloromethane (3×20 ml). The combined organic layers are dried with $MgSO_4$, filtered and evaporated. Recrystallisation from ethyl acetate (5 ml) yields the title compound as a colorless solid ($R_1$=$CH_2$—C(O)—OEt, $R_2$=3,4,5-trimethoxybenzyl, n=0).

Example 11

Ethyl-2-[2-oxo-3-(3,4,5-trimethoxybenzyl)-3-benzimidazolyl)]acetic Acid

Ethyl-2-[2-oxo-3-(3,4,5-trimethoxybenzyl)-3-benzimidazolyl)]acetate (4.19 mmol, 1.68 g) (example 10) is added to potassium hydroxide (13.41 mmol, 0.75 g) in ethanol (10 ml), and the mixture is stirred at reflux for 2 hours. The solvent is evaporated and water (40 ml) is added. The pH is adjusted to 1–2 with concentrated hydrochloric acid. The colorless precipitate is filtered off and dried in vacuo to yield the title compound ($R_1$=$CH_2$—C(O)—OH, $R_2$=3,4,5-trimethoxybenzyl, n=0).

Example 12

2-[2-Oxo-3-(3,4,5-trimethoxybenzyl-)3-hydrobenzimidazolyl]N-benzylethanamide 2-(2-oxo-3-(3,4,5-trimethoxybenzyl)-3-hydrobenzimidazolyl)acetic acid (1.77 mmol, 0.66 g) (example 11) in DMA (5 ml) is charged with 1-(3-dimethylaminopropyl)-3-ethyl-carbodiimide HCl (2.66 mmol, 0.51 g). Benzylamine (2.48 mmol, 0.27 ml) is added to the suspension, and the mixture is stirred at room temperature for 17 hours. The solution is added dropwise into ice (50 g), and the colorless precipitate is filtered off and dried in vacuo. Recrystallisation from ethyl acetate yields the title product ($R_1$=—$CH_2$—C(O)—$NHR_5$, x=1, $R_5$=benzyl, $R_2$=3,4,5-trimethoxybenzyl, n=0).

Example 13

Ethyl [3-(3-(3,4,5-Trimethoxybenzyl)-2-oxo-benzimidazolyl)]propionate

Sodium hydride (14.1 mmol, 0.56 g, 60% mineral oil) is dissolved in dimethylacetamide (10 ml). 1-(3,4,5-trimethoxybenzyl)-3-hydrobenzimidazol-2-one (9.1 mmol, 2.86 g) (example 10) in dimethylacetamide (10 ml) is added dropwise to the ice cooled solution which is stirred for 1 hour. Ethyl 3-bromopropionate (14.1 mmol, 1.79 ml, 2.53 g) in dimethyl-acetamide (5 ml) is added, and the mixture is stirred 24 hours at room temperature. The solution is added dropwise into ice (300 g), and the precipitate is filtered off, added to a 1:1 dichloromethane/water mixture and is extracted with dichloromethane (3×20 ml). The combined organic layers are dried with $MgSO_4$, filtered and evaporated. Recrystallisation from ethyl acetate (5 ml) yields the title compound ($R_1$=$(CH_2)_2$—C(O)—OEt, $R_2$=3,4,5-trimethoxybenzyl, x=2, n=0).

Example 14

3-[2-Oxo-3-(3,4,5-trimethoxybenzyl) benzimidazolyl)]propionic Acid

Ethyl 3-[2-oxo-3-(3,4,5-trimethoxybenzyl)-benzimidazolyl)]propionate (4.19 mmol, 1.74 g) (example 13) is added to potassium hydroxide (13.41 mmol, 0.75 g) in ethanol (10 ml), and the mixture is stirred at reflux for 2 hours. The solvent is evaporated and water (40 ml) is added. The pH is adjusted to 1–2 with concentrated hydrochloric acid. The colorless precipitate is filtered off and dried in vacuo to yield the title compound ($R_1$==$(CH_2)_2$—C(O)—OH, $R_2$=3,4,5-trimethoxybenzyl, x=2, n=0).

Example 19

3-[2-Oxo-3-(3,4,5-trimethoxybenzyl) benzimidazolyl]N-benzyl-propanamide

3-[2-Oxo-3-(3,4,5-trimethoxybenzyl)-benzimidazolyl] propionic acid (1.77 mmol, 0.69 g) (example 14) in DMA (5 ml) is charged with 1-(3-dimethylaminopropyl)-3-ethyl-carbodiimide HCl (2.66 mmol, 0.51g). Benzylamine (2.48 mmol, 0.27 ml) is added to the suspension, and the mixture is stirred at room temperature for 17 hours. The solution is added dropwise into ice (50 g) and the colorless precipitate is filtered off and dried in vacuo. Recrystallisation from ethyl acetate yields the title product. ($R_1$=$(CH_2)_2$—C(O)—$NHR_5$, x=2. $R_5$=benzyl, $R_2$=3,4,5-trimethoxybenzyl, n=0).

The following examples are obtainable from the procedures of Example 1–15. and are also commercially available from Sarco chemical Co.:

Example 16

N-(3,5-Dimethoxybenzyl)-N-carbamoylmethyl-2-[2-oxo-3-(2,3,4,5,6-pentafluorobenzyl-7-benzoyl-3-hydrobenzimidazolyl]ethanamide ($R_1$=—$(CH_2)_x$—C(O)—$NR_6R_7$, $R_2$=2,3,4,5,6-pentafluorobenzyl-, $R_3$=benzoyl, $R_6$=3,5-dimethoxybenzyl, $R_7$=carbamoylmethyl, n=1, x=1).

Example 17

Ethyl 4-[N-carbamoylmethyl-2-(2-oxo-7-benzoyl-3-hydrobenzimidazolyl)acetylamino]benzoate ($R_1$=—$(CH_2)_x$—C(O)—$NR_6R_7$, $R_2$=H, $R_3$=benzoyl, $R_6$=4-ethoxycarbonylphenyl, $R_7$=carbamoylmethyl, n=1, x=1).

Example 18

N-(4-Diethylaminophenyl)-N-carbamoylmethyl-2-[5-nitro-2-oxo-3-hydro-benzimidazolyl]ethanamide ($R_1$=—$(CH_2)_x$—C(O)—$NR_6R_7$, $R_2$=H, $R_3$=nitro, $R_6$=4-diethylaminophenyl, $R_7$=carbamoylmethyl, n=1, x=1)

Example 19

N-(3,5-Dimethoxybenzyl)-N-carbamoylmethyl-2-[5-nitro-2-oxo-3-(prop-2-enyl)-3-hydro-benzimidazolyl]ethanamide ($R_1$=—$(CH_2)_x$—C(O)—$NR_6R_7$, $R_2$=2-propenyl, $R_3$=nitro, $R_6$=3,5-dimethoxybenzyl, $R_7$=carbamoylmethyl, n=1, x=1).

Example 20

N-(4-Diethylaminophenyl)-N-carbamoylmethyl-2-[5-nitro-2-oxo-3-(prop-2-enyl)-3-hydro-benzimidazolyl]ethanamide ($R_1$=—$(CH_2)_x$—C(O)—$NR_6R_7$, $R_2$=2-propenyl, $R_3$=nitro, $R_6$=4-diethylaminophenyl, $R_7$=carbamoylmethyl, n=1, x=1)

Example 21

N-(4-Diethylaminophenyl)-N-carbamoylmethyl-2-[7-benzoyl-2-oxo-3-(prop-2-enyl)-3-hydro-benzimidazolyl]ethanamide ($R_1$=—$(CH_2)_x$—C(O)—$NR_6R_7$, $R_2$=2-propenyl, $R_3$=benzoyl, $R_6$=4-diethylaminophenyl, $R_7$=carbamoylmethyl, n=1, x=1).

Example 22

N-(4-Diethylaminophenyl)-N-carbamoylmethyl-2-[2-oxo-3-(prop-2-enyl)-5-trifluoromethyl-3-hydrobenzimidazolyl]ethanamide ($R_1$=—$(CH_2)_x$—C(O)—$NR_6R_7$, $R_2$=2-propenyl, $R_3$=trifluoromethyl, $R_6$=4-diethylaminophenyl, $R_7$=carbamoylmethyl, n=1, x=1).

Example 23

N-(2-tetrahydrofuranylmethyl)-N-carbamoylmethyl-2-[7-benzoyl-2-oxo-3-)prop-2-enyl) hydrobenzimidazolyl]ethanamide ($R_1$=—$(CH_2)_x$—C(O)—$NR_6R_7$, $R_2$=2-propenyl, $R_3$=benzoyl, $R_6$=2-tetrahydrofuranylmethyl, $R_7$=carbamoylmethyl, n=1, x=1).

Example 24

N-(3,5-Dimethoxybenzyl)-N-carbamoylmethyl-2-[3-benzyl-5-nitro-2-oxo-3-hydro-benzimidazolyl] ethanamide ($R_1$=—$(CH_2)_x$—C(O)—$NR_6R_7$, $R_2$=benzyl, $R_3$=nitro, $R_6$=3,5-dimethoxybenzyl, $R_7$=carbamoylmethyl, n=1, x=1).

Example 25

N-(3,5-Dimethoxybenzyl)-N-carbamoylmethyl-2-[7-benzoyl-3-benzyl-2-oxo-3-hydro-benzimidazolyl] ethanamide ($R_1$=—$(CH_2)_x$—C(O)—$NR_6R_7$, $R_2$=benzyl, $R_3$=benzoyl, $R_6$=3,5-dimethoxybenzyl, $R_7$=carbamoylmethyl, n=1, x=1).

Example 26

N-Benzyl-N-carbamoylmethyl-2-[7-benzoyl-3-benzyl-2-oxo-3-hydro-benzimidazolyl]ethanamide ($R_1$=—($CH_2$)—C(O)—$NR_6R_7$, $R_2$=benzyl, $R_3$=benzoyl, $R_6$=benzyl, $R_7$=carbamoylmethyl, n=1, x=1).

Example 27

N-(3,5-Dimethoxybenzyl)-N-carbamoylmethyl-2-[3-ethyl-5-methyl-2-oxo-3-hydro-benzimidazolyl]ethanamide ($R_1$=—($CH_2$)$_x$—C(O)—$NR_6R_7$, $R_2$=ethyl, $R_3$=methyl, $R_6$=3,5-dimethoxybenzyl, $R_7$=carbamoylmethyl, n=1, x=1).

Example 28

N-(3-bromobenzyl)-N-carbamoylmethyl-2-[3-ethyl-5-nitro-2-oxo-3-hydro-benzimidazolyl]ethanamide ($R_1$=—($CH_2$)$_x$—C(O)—$NR_6R_7$, $R_2$=ethyl, $R_3$=nitro, $R_6$=3-bromobenzyl, $R_7$=carbamoylmethyl, n=1, x=1).

Example 29

N-benzyl-N-carbamoylmethyl-2-[3-ethyl-5-methoxycarbonyl-2-oxo-3-hydro-benzimidazolyl]ethanamide ($R_1$=—($CH_2$)$_x$—C(O)—$NR_6R_7$, $R_2$=ethyl, $R_3$=methoxycarbonyl, $R_6$=benzyl, $R_7$=carbamoylmethyl, n=1, x=1).

Example 30

[N-carbamoylmethyl-N-(4'-ethoxycarbonylphenyl)-2-(5,6-dimethyl-3-ethyl-2-oxobenzimidazolyl)ethanamide ($R_1$=—($CH_2$)$_x$—C(O)—$NR_6R_7$, $R_2$=ethyl, $R_3$=methyl, $R_6$=4-ethoxycarbonylphenyl, $R_7$=carbamoylmethyl, n=2, x=1).

Example 31

[N-carbamoylmethyl-N-(4'-ethoxycarbonylphenyl)-2-(3-ethyl-5-nitro-2-oxobenzimidazolyl)]ethanamide ($R_1$=—($CH_2$)$_x$—C(O)—$NR_6R_7$, $R_2$=ethyl, $R_3$=nitro, $R_6$=4-ethoxycarbonylphenyl, $R_7$=carbamoylmethyl, n=1, x=1).

Example 32

[N-carbamoylmethyl-N-(4'-ethoxycarbonylphenyl-2-(3-ethyl-5-methyl-2-oxobenzimidazolyl)]ethanamide ($R_1$=—($CH_2$)$_x$—C(O)—$NR_6R_7$, $R_2$=ethyl, $R_3$=methyl, $R_6$=4-ethoxycarbonylphenyl, $R_7$=carbamoylmethyl, n=1, x=1).

Example 32

[N-carbamoylmethyl N-(4'-ethoxycarbonylpiperidinyyl)-2-(7-benzoyl-3-ethyl-2-oxobenzimidazolyl)]ethanamide ($R_1$=—($CH_2$)$_x$—C(O)—$NR_7$, $R_2$=ethyl, $R_3$=benzoyl, $R_6$=N-ethoxycarbonylpiperidin-4-yl, $R_7$=carbamoylmethyl, n=1, x=1).

Example 33

N-(4-diethylaminophenyl)-N-carbamoylmethyl-2-[5,6-dimethyl-3-ethyl-2-oxobenzimidazolyl]ethanamide ($R_1$=—($CH_2$)$_x$—C(O)—$NR_6R_7$, $R_2$=ethyl, $R_3$=methyl, $R_6$=4-diethylaminophenyl, $R_7$=carbamoylmethyl, n=2, x=1).

Example 34

N-(4-diethylaminophenyl)-N-carbamoylmethyl-2-[3-ethyl-5-nitro-2-oxobenzimidazolyl]ethanamide ($R_1$=—($CH_2$)$_x$—C(O)—$NR_6R_7$, $R_2$=ethyl, $R_3$=nitro, $R_6$=4-diethylaminophenyl, $R_7$=carbamoylmethyl, n=1, x=1).

Example 35

N-(4-diethylaminophenyl)-N-carbamoylmethyl-2-[7-benzoyl-3-ethyl-2-oxobenzimidazolyl]ethanamide ($R_1$=—($CH_2$)$_x$—C(O)—$NR_6R_7$, $R_2$=ethyl, $R_3$=benzoyl, $R_6$=4-diethylaminophenyl, $R_7$=carbamoylmethyl, n=1, x=1).

Example 36

N-(4-diethylaminophenyl)-N-carbamoylmethyl-2-[3-ethyl-6-methoxycarbonyl-2-oxobenzimidazolyl]ethanamide ($R_1$=—($CH_2$)$_x$—C(O)—$NR_6R_7$, $R_2$=ethyl, $R_3$=methoxcarbonyl, $R_6$=4-diethylaminophenyl, $R_7$=carbamoylmethyl, n=1, x=1).

Example 37

N-(4-diethylaminophenyl)-N-carbamoylmethyl-2-[3-ethyl-2-oxo-5-trifluoromethylbenzimidazolyl]ethanamide ($R_1$=—($CH_2$)$_x$—C(O)—$NR_6R_7$, $R_2$=ethyl, $R_3$=trifluoromethyl, $R_6$=4-diethylaminophenyl, $R_7$=carbamoylmethyl, n=1, x=1).

Example 38

N-(4-diethylaminophenyl)-N-carbamoylmethyl-2-[3-ethyl-6-fluoro-2-oxobenzimidazolyl]ethanamide ($R_1$=—($CH_2$)$_x$—C(O)—$NR_6R_7$, $R_2$=ethyl, $R_3$=fluoro, $R_6$=4-diethylaminophenyl, $R_7$=carbamoylmethyl, n=1, x=1).

Example 39

N-(4-Diethylaminophenyl)-N-carbamoylmethyl-2-[3-ethyl-5-methyl-2-oxobenzimidazolyl]ethanamide ($R_1$=—($CH_2$)$_x$—C(O)—$NR_6R_7$, $R_2$=ethyl, $R_3$=methyl, $R_6$=4-diethylaminophenyl, $R_7$=carbamoylmethyl, n=1, x=1).

Example 40

N-(2-tetrahydrofuranylmethyl)-N-carbamoylmethyl-2-[5,6-dimethyl-2-oxo-3-ethylbenzimidazolyl]ethanamide ($R_1$=—($CH_2$)$_x$—C(O)—$NR_6R_7$, $R_2$=ethyl, $R_3$=methyl, $R_6$=2-tetrahydrofuranylmethyl, $R_7$=carbamoylmethyl, n=2, x=1).

Example 41

N-(2-tetrahydrofuranylmethyl)-N-carbamoylmethyl-
2-[5-nitro-2-oxo-3-ethyl-3-hydrobenzimidazolyl]
ethanamide ($R_1$=—$(CH_2)_x$—C(O)—$NR_6R_7$, $R_2$=ethyl, $R_3$=nitro, $R_6$=2-tetrahydrofuranylmethyl, $R_7$=carbamoylmethyl, n=1, x=1).

Example 42

N-(2-tetrahydrofuranylmethyl)-N-carbamoylmethyl-
2-[7-benzoyl-2-oxo-3-ethylbenzimidazolyl]
ethanamide ($R_1$=—$(CH_2)_x$—C(O)—$NR_6R_7$, $R_2$=ethyl, $R_3$=benzoyl, $R_6$=2-tetrahydrofuranylmethyl, $R_7$=carbamoylmethyl, n=1, x=1).

Example 43

N-(2-tetrahydrofuranylmethyl)-N-carbamoylmethyl-
2-[6-methoxycarbonyl-2-oxo-3-ethylbenzimidazolyl]
ethanamide ($R_1$=—$(CH_2)_x$—C(O)—$NR_6R_7$, $R_2$=ethyl, $R_3$=methoxycarbonyl, $R_6$=2-tetrahydrofuranylmethyl, $R_7$=carbamoylmethyl, n=1, x=1).

Example 44

N-(2-tetrahydrofuranylmethyl)-N-carbamoylmethyl-
2-[2-oxo-3-ethyl-5-trifluoromethylbenzimidazolyl]
ethanamide ($R_1$=—$(CH_2)_x$—C(O)—$NR_6R_7$, $R_2$=ethyl, $R_3$=trifluoromethyl, $R_6$=2-tetrahydrofuranylmethyl, $R_7$=carbamoylmethyl, n=1, x=1).

Example 45

2-{[N-(3,5-dimethoxybenzyl)-N-carbamoylmethyl]-
3-(ethyl-2'-acetate-5-nitro-2-oxobenzimidazol-3-yl]
ethyl Acetate ($R_1$=—$(CH_2)_x$—C(O)—$NR_6R_7$, $R_2$=acetoxyethyl, $R_3$=nitro, $R_6$=3,5-dimethoxybenzyl, $R_7$=carbamoylmethyl, n=1, x=1).

Example 46

N-benzyl-N-carbamoylmethyl-2-[7-benzoyl-2-oxo-
3-(2,3,4,5,6-pentafluorobenzyl)benzimidazolyl]
ethanamide ($R_1$=—$(CH_2)_x$—C(O)—$NR_6R_7$, $R_2$=2,3,4,5,6-pentafluorobenzyl, $R_3$=benzoyl, $R_6$=3,5-dimethoxybenzyl, $R_7$=carbamoylmethyl, n=1, x=1).

Example 47

2-{[N-(4-Diethylaminophenyl)-N-
carbamoylmethyl]-3-ethyl-2'-acetate)-5-nitro-2-
oxobenzimidazol-3-yl]ethanamide ($R_1$=—$(CH_2)_x$—C(O)—$NR_6R_7$, $R_2$=2'-ethyl-1'-acetate, $R_3$=nitro, $R_6$=4-diethylaminophenyl, $R_7$=carbamoylmethyl, n=1, x=1).

Example 48

2-{[N-(4-Diethylaminophenyl)-N-carbamoylmethyl]
carbamoylmethyl-7-benzoyl-2-oxo-3-
hydrobenzimidazol-3-yl]ethanamide ($R_1$=—$(CH_2)_x$—C(O)—$NR_6R_7$, $R_2$=2'-ethyl-1'-acetate, $R_3$=benzoyl, $R_6$=4-diethylaminophenyl, $R_7$=carbamoylmethyl, n=1, x=1).

Example 49

2-{[N-(4-Diethylaminophenyl)-N-
carbamoylmethyl]-3-(ethyl-2'-acetate-2-oxo-5-
trifluoromethylbenzimidazol-3-yl]ethanamide ($R_1$=—$(CH_2)_x$—C(O)—$NR_6R_7$, $R_2$=acetoxyethyl, $R_3$=trifluoromethyl, $R_6$=4-diethyl-aminophenyl, $R_7$=carbamoylmethyl, n=1, x=1).

Example 50

N-(3,5-Dimethoxybenzyl)-N-carbamoylmethyl-2-[5-
nitro-2-oxo-3-cyanomethyl-3-hydrobenzimidazolyl]
ethanamide ($R_1$=—$(CH_2)_x$—C(O)—$NR_6R_7$, $R_2$=cyanomethyl, $R_3$=nitro, $R_6$=3,5-dimethoxybenzyl, $R_7$=carbamoylmethyl, n=1, x=1).

Example 51

N-benzyl-N-carbamoylmethyl-2-[2-oxo-3-(2,3,4,5,6-
pentafluorobenzyl)-5-
trifluoromethylbenzimidazolyl]ethanamide ($R_1$=—$(CH_2)_x$—C(O)—$NR_6R_7$, $R_2$=2,3,4,5,6-pentafluorobenzyl, $R_3$=trifluoromethyl, $R_6$=3,5-dimethoxybenzyl, $R_7$=carbamoylmethyl, n=1, x=1).

Example 52

[Ethyl-4-[N-carbamoylmethyl-N-[4'-(N'-
ethoxycarbonyl-piperdinyl)]-2-(7-benzoyl-3-
cyanomethyl-2-oxobenzimidazolyl)]ethanamide ($R_1$=—$(CH_2)_x$—C(O)—$NR_6R_7$, $R_2$=cyanomethyl, $R_3$=benzoyl, $R_6$=N-ethoxycarbonyl-piperidin-4-yl, $R_7$=carbamoylmethyl, n=1, x=1).

Example 53

Ethyl-4-[N-carbamoylmethyl-N-[4'-(N'-
ethoxycarbonyl-piperdinyl)]2-(3-cyanomethyl-2-
oxo-5-trifluoromethylbenzimidazolyl)]ethanamide ($R_1$=—$(CH_2)_x$—C(O)—$NR_6R_7$, $R_2$=cyanomethyl, $R_3$=trifluoromethyl, $R_6$=N-ethoxycarbonyl-piperidin-4-yl, $R_7$=carbamoylmethyl, n=1, x=1).

Example 54

N-(4-diethylaminophenyl)-N-carbamoylmethyl-2-[5,
6-dimethyl-2-oxo-3-hydrobenzimidazolyl]
ethanamide ($R_1$=—$(CH_2)_x$—C(O)—$NR_6R_7$, $R_2$=H, $R_3$=methyl, $R_6$=4-diethylaminophenyl, $R_7$=carbamoylmethyl, n=2, x=1).

Example 55

N-(4-diethylaminophenyl)-N-carbamoylmethyl-2-[5-Nitro-2-oxo-3-cyanomethylbenzimidazolyl]ethanamide ($R_1$=—$(CH_2)_x$—C(O)—$NR_6R_7$, $R_2$=cyanomethyl, $R_3$=nitro, $R_6$=4-diethylaminophenyl, $R_7$=carbamoylmethyl, n=1, x=1).

Example 56

N-(4-diethylaminophenyl)-N-carbamoylmethyl-2-[7-benzoyl-2-oxo-3-cyanomethylbenzimidazolyl]ethanamide ($R_1$=—$(CH_2)_x$—C(O)—$NR_6R_7$, $R_2$=cyanomethyl, $R_3$=benzoyl, $R_6$=4-diethylaminophenyl, $R_7$=carbamoylmethyl, n=1, x=1).

Example 57

N-(4-diethylaminophenyl)-N-carbamoylmethyl-2-[3-cyanomethyl-6-methoxycarbonyl-2-oxobenzimidazolyl]ethanamide ($R_1$=—$(CH_2)_x$—C(O)—$NR_6R_7$, $R_2$=cyanomethyl, $R_3$=methoxycarbonyl, $R_6$=4-diethylaminophenyl, $R_7$=carbamoylmethyl, n=1, x=1).

Example 58

N-(4-diethylaminophenyl)-N-carbamoylmethyl-2-[3-cyanomethyl-2-oxo-5-trifluoromethylbenzimidazolyl]ethanamide ($R_1$=—$(CH_2)_x$—C(O)—$NR_6R_7$, $R_2$=cyanomethyl, $R_3$=trifluoromethyl, $R_6$=4-diethylaminophenyl, $R_7$=carbamoylmethyl, n=1, x=1).

Example 59

N-(4-diethylaminophenyl)-N-carbamoylmethyl-2-[3-cyanomethyl-2-oxo-5-methylbenzimidazolyl]ethanamide ($R_1$—$(CH_2)_x$—C(O)—$NR_6R_7$, $R_2$=cyanomethyl, $R_3$=methyl, $R_6$=4-diethylaminophenyl, $R_7$=carbamoylmethyl, n=1, x=1)

Example 60

N-(2-tetrahydrofuranylmethyl)-N-carbamoylmethyl-2-[3-cyanomethyl-2-oxo-5-nitrobenzimidazolyl]ethanamide ($R_1$=—$(CH_2)_x$—C(O)—$NR_6R_7$, $R_2$=cyanomethyl, $R_3$=nitro, $R_6$=4-diethylaminophenyl, $R_7$=carbamoylmethyl, n=1, x=1).

Example 61

N-(2-tetrahydrofuranylmethyl)-N-carbamoylmethyl-2-[7-benzoyl-3-cyanomethyl-2-oxobenzimidazolyl]ethanamide ($R_1$=—$(CH_2)_x$—C(O)—$NR_6R_7$, $R_2$=cyanomethyl, $R_3$=benzoyl, $R_6$=2-tetrahydrofuranyl, $R_7$=carbamoylmethyl, n=1, x=1).

Example 62

N-(Cyclohexylmethyl)-N-carbamoylmethyl-2-[5,6-dimethyl-3-(2,3,4,5,6-pentafluoro-benzyl)-2-oxobenzimidazolyl]ethanamide ($R_1$=—$(CH_2)_x$—C(O)—$NR_6R_7$, $R_2$=2,3,4,5,6-pentafluorobenzyl, $R_3$=methyl, $R_6$=4-diethylaminophenyl, $R_7$=carbamoylmethyl, n=2, x=1).

Example 63

N-(4-diethylaminophenyl)-N-carbamoylmethyl-2-[3-(ethyl-2'-benzoate)-2-oxo-5,6-dimethylbenzimidazolyl]ethanamide ($R_1$=—$(CH_2)_x$—C(O)—$NR_7$, $R_2$=benzoyloxyethyl, $R_3$=methyl, $R_6$=4-diethylaminophenyl, $R_7$=carbamoylmethyl, n=2, x=1).

Example 64

N-(2-methylpropyl)-N-carbamoylmethyl-2-[3-(ethyl-2'-benzoate)-6-methoxycarbonyl-2-oxobenzimidazolyl]ethanamide ($R_1$=—$(CH_2)_x$—C(O)—$NR_6R_7$, $R_2$=2'-ethyl-1'-benzoate, $R_3$=methoxycarbonyl, $R_6$=2-methylpropyl, $R_7$=carbamoylmethyl, n=1, x=1).

Example 65

N-(4-diethylaminophenyl)-N-carbamoylmethyl-2-[3-(ethyl-2'-benzoate)-2-oxo-5-trifluoromethylbenzimidazolyl]ethanamide ($R_1$=—$(CH_2)_x$—C(O)—$NR_6R_7$, $R_2$=2'-ethyl-1'-benzoate, $R_3$=trifluoromethyl, $R_6$=4-diethylaminophenyl, $R_7$=carbamoylmethyl, n=1, x=1).

Example 66

N-(4-diethylaminophenyl)-N-carbamoylmethyl-2-[3-(ethyl-2'-benzoate)-5-methyl-2-oxobenzimidazolyl]ethanamide ($R_1$=—$(CH_2)_x$—C(O)—$NR_6R_7$, $R_2$=2'-ethyl-1'-benzoate, $R_3$=methyl, $R_6$=4-diethylamino-phenyl, $R_7$=carbamoylmethyl, n=1, x=1).

Example 67

N-(2-tetrahydrofuranylmethyl)-N-carbamoylmethyl-2-[3-(ethyl-2'-benzoate-5,6-dimethyl-2-oxobenzimidazolyl]ethanamide ($R_1$=—$(CH_2)_x$—C(O)—$NR_6R_7$, $R_2$=2'-ethyl-1'-benzoate, $R_3$=methyl, $R_6$=2-tetrahydrofuranylmethyl, $R_7$=carbamoylmethyl, n=2, x=1).

Example 68

[N-carbamoylmethyl-N-[4'-(N'-ethoxycarbonyl-piperdinyl)]-2-(5,6-Dimethyl-2-oxo-3-(2,3,4,5,6-pentafluorobenzyl)benzimidazolyl)ethanamide ($R_1$=—$(CH_2)_x$—C(O)—$NR_6R_7$, $R_2$=2,3,4,5,6-pentafluorobenzyl, $R_3$=methyl, $R_6$=N-ethoxycarbonyl-piperidin-4-yl, $R_7$=carbamoylmethyl, n=2, x=1).

Example 69

N-benzyl-N-carbamoylmethyl-2-[3-(2-methoxy-5-nitrobenzyl)-5-nitro-2-oxobenzimidazolyl]ethanamide ($R_1$=—$(CH_2)_x$—C(O)—$NR_6R_7$, $R_2$=2-methoxy-5-nitrobenzyl, $R_3$=nitro, $R_6$=benzyl, $R_7$=carbamoylmethyl, n=1, x=1).

Example 70

N-benzyl-N-carbamoylmethyl-2-[3-(2-methoxy-5-nitrobenzyl)-6-methoxycarbonyl-2-oxobenzimidazolyl]ethanamide ($R_1$=—$(CH_2)_x$—C(O)—$NR_6R_7$, $R_2$=2-methoxy-5-nitrobenzyl, $R_3$=methoxycarbonyl, $R_6$=benzyl, $R_7$=carbamoylmethyl, n=1, x=1).

Example 71

N-benzyl-N-carbamoylmethyl-2-[6-fluoro-3-(2-methoxy-5-nitrobenzyl)-2-oxobenzimidazolyl]ethanamide ($R_1$=—$(CH_2)_x$—C(O)—$NR_6R_7$, $R_2$=2-methoxy-5-nitrobenzyl, $R_3$=fluoro, $R_6$=benzyl, $R_7$=carbamoylmethyl, n=1, x=1).

Example 72

[N-carbamoylmethyl]-N-[4'-(N'-ethoxycarbonyl-piperidinyl)]-2-(7-benzoyl-2-oxo-3-(2,3,4,5,6-pentafluorobenzyl)benzimidazolyl)ethanamide ($R_1$=—$(CH_2)_x$—C(O)—$NR_6R_7$, $R_2$=2,3,4,5,6-pentafluorobenzyl, $R_3$=benzoyl, $R_6$=N-ethoxycarbonyl-piperidin-4-yl, $R_7$=carbamoylmethyl, n=1, x=1).

Example 73

[N-carbamoylmethyl-N-[4'-(N'-ethoxycarbonyl-piperidinyl)]—2-(5-methyl-2-oxo-3-(2,3,4,5,6-pentafluorobenzyl)benzimidazolyl)ethanamide ($R_1$=—$(CH_2)_x$—C(O)—$NR_6R_7$, $R_2$=2,3,4,5,6-pentafluorobenzyl, $R_3$=methyl, $R_6$=N-ethoxycarbonyl-piperidin-4-yl, $R_7$=carbamoylmethyl, n=1, x=1).

Example 74

N-(4-diethylaminophenyl)-N-carbamoylmethyl-2-[5,6-dimethyl-2-oxo-3-(2,3,4,5,6-pentafluorobenzyl)benzimidazolyl]ethylbenzamide ($R_1$=—$(CH_2)_x$—C(O)—$NR_6R_7$, $R_2$=2,3,4,5,6-pentafluorobenzyl, $R_3$=methyl, $R_6$=4-diethylaminophenyl, $R_7$=carbamoylmethyl, n=2, x=1).

Example 75

[N-carbamoylmethyl-N-[4'-(N'-ethoxycarbonylphenyl)]-2-[(5-methyl-3-(2-methoxy-5-nitrobenzyl)-2-oxobenzimidazolyl]ethanamide ($R_1$=—$(CH_2)_x$—C(O)—$NR_6R_7$, $R_2$=2-methoxy-5-nitrobenzyl, $R_3$=methyl, $R_6$=4-ethoxycarbonylphenyl, $R_7$=carbamoylmethyl, n=1, x=1).

Example 76

N-(4-diethylaminophenyl)-N-carbamoylmethyl-2-[6-methoxycarbonyl-2-oxo-3-(2,3,4,5,6-pentafluorobenzyl)benzimidazolyl]ethanamide ($R_1$=—$(CH_2)_x$—C(O)—$NR_7R_7$, $R_2$=2,3,4,5,6-pentafluorobenzyl, $R_3$=methoxycarbonyl, $R_6$=4-diethylaminophenyl, $R_7$=carbamoylmethyl, n=1, x=1)

Example 77

[N-carbamoylmethyl-N-[4'-(N'-ethoxycarbonyl-piperidinyl)]—2-(7-benzoyl-2-oxo-3-(2-methoxy-5-nitrobenzyl)benzimidazolyl)ethanamide ($R_1$=—$(CH_2)_x$—C(O)—$NR_7$, $R_2$=2-methoxy-5-nitrobenzyl, $R_3$=benzoyl, $R_6$=N-ethoxycarbonyl-piperidin-4-yl, $R_7$=carbamoylmethyl, n=1, x=1).

Example 78

N-benzyl-N-carbamoylmethyl-2-[2-oxo-3-(2,3,4,5,6-pentafluorobenzyl)-5-trifluoromethylbenzimidazolyl]ethanamide ($R_1$=—$(CH_2)_x$—C(O)—$NR_6R_7$, $R_2$=2,3,4,5,6-pentafluorobenzyl, $R_3$=trifluoromethyl, $R_6$=benzyl, $R_7$=carbamoylmethyl, n=1, x=1).

Example 79

N-(4-diethylaminophenyl)-N-carbamoylmethyl-2-[7-benzoyl-3-(2-methoxy-5-nitrobenzyl)-2-oxobenzimidazolyl]ethanamide ($R_1$=—$(CH_2)_x$—C(O)—$NR_6R_7$, $R_2$=2-methoxy-5-nitrobenzyl, $R_3$=benzoyl, $R_6$=4-diethylaminophenyl, $R_7$=carbamoylmethyl, n=1, x=1).

Example 80

N-(4-diethylaminophenyl)-N-carbamoylmethyl-2-[6-fluoro-3-(2-methoxy-5-nitrobenzyl)-2-oxobenzimidazolyl]ethanamide ($R_1$=—$(CH_2)_x$—C(O)—$NR_6R_7$, $R_2$=2-methoxy-5-nitrobenzyl, $R_3$=fluoro, $R_6$=4-diethylaminophenyl, $R_7$=carbamoylmethyl, n=1, x=1).

Example 81

N-(4-diethylaminophenyl)-N-carbamoylmethyl-2-[3-(2-methoxy-5-nitrobenzyl)-5-methyl-2-oxobenzimidazolyl]ethanamide ($R_1$=—$(CH_2)_x$—C(O)—$NR_6R_7$, $R_2$=2-methoxy-5-nitrobenzyl, $R_3$=methyl, $R_6$=4-diethylaminophenyl, $R_7$=carbamoylmethyl, n=1, x=1).

Example 82

N-(2-tetrahydrofuranylmethyl)-N-carbamoylmethyl-2-[5,6-dimethyl-3-(2-methoxy-5-nitrobenzyl)-2-oxobenzimidazolyl]ethanamide ($R_1$=—$(CH_2)_x$—C(O)—$NR_6R_7$, $R_2$=2-methoxy-5-nitrobenzyl, $R_3$=methyl, $R_6$=2-tetrahydrofuranylmethyl, $R_7$=carbamoylmethyl, n=2, x=1).

Example 83

N-(2-tetrahydrofuranylmethyl)-N-carbamoylmethyl-2-[3-(2-methoxy-5-nitrobenzyl)-5-nitro-2-oxobenzimidazolyl]ethanamide ($R_1$=—($CH_2$)$_x$—C(O)—N$R_6R_7$, $R_2$=2-methoxy-5-nitrobenzyl, $R_3$=nitro, $R_6$=2-tetrahydrofuranylmethyl, $R_7$=carbamoylmethyl, n=1, x=1).

Example 84

N-(2-tetrahydrofuranylmethyl)-N-carbamoylmethyl-2-[7-benzoyl-3-(3-methoxybenzyl)-5-nitro-2-oxobenzimidazolyl]ethanamide ($R_1$=—($CH_2$)$_x$—C(O)—N$R_6R_7$, $R_2$=3-methoxybenzyl, $R_3$=benzoyl, $R_6$=2-tetrahydrofuranylmethyl, $R_7$=carbamoylmethyl, n=1, x=1).

Example 85

N-(2-tetrahydrofuranylmethyl)-N-carbamoylmethyl-2-[7-benzoyl-3-(2-methoxy-5-nitrobenzyl)-2-oxobenzimidazolyl]ethanamide ($R_1$=—($CH_2$)$_x$—C(O)—N$R_6R_7$, $R_2$=2-methoxy-5-nitrobenzyl, $R_3$=benzoyl, $R_6$=2-tetrahydrofuranylmethyl, $R_7$=carbamoylmethyl, n=1, x=1).

Example 86

N-(2-tetrahydrofuranylmethyl)-N-carbamoylmethyl-2-[6-methoxycarbonyl-3-(2-methoxy-5-nitrobenzyl)-2-oxobenzimidazolyl]ethanamide ($R_1$=—($CH_2$)$_x$—C(O)—N$R_6R_7$, $R_2$=2-methoxy-5-nitrobenzyl, $R_3$=methoxycarbonyl, $R_6$=2-tetrahydrofuranylmethyl, $R_7$=carbamoylmethyl, n=1, x=1).

Example 87

N-(2-tetrahydrofuranylmethyl)-N-carbamoylmethyl-2-[3-(2-methoxy-5-nitrobenzyl)-6-trifluoromethyl-2-oxobenzimidazolyl]ethanamide ($R_1$=—($CH_2$)$_x$—C(O)—N$R_6R_7$, $R_2$=2-methoxy-5-nitrobenzyl, $R_3$=trifluoromethyl, $R_6$=2-tetrahydrofuranylmethyl, $R_7$=carbamoylmethyl, n=1, x=1).

Example 88

N-(3-bromobenzyl)-N-carbamoylmethyl-2-[3-(3-phenyloxypropyl)-5-nitro-2-oxobenzimidazolyl]ethanamide ($R_1$=—($CH_2$)$_x$—C(O)—N$R_6R_7$, $R_2$=3-phenyloxypropyl, $R_3$=nitro, $R_6$=3-bromobenzyl, $R_7$=carbamoylmethyl, n=1, x=1).

Example 89

N-(2-tetrahydrofuranylmethyl)-N-carbamoylmethyl-2-[5,6-dimethyl-2-oxo-3-(2,3,4,5,6-pentafluorobenzyl)benzimidazolyl]ethanamide ($R_1$=—($CH_2$)$_x$—C(O)—N$R_6R_7$, $R_2$=2,3,4,5,6-pentafluorobenzyl, $R_3$=methyl, $R_6$=2-tetrahydrofuranylmethyl, $R_7$=carbamoylmethyl, n=2, x=1).

Example 90

N-benzyl-N-carbamoylmethyl-2-[3-(3-phenyloxypropyl)-5-nitro-2-oxobenzimidazolyl]ethanamide ($R_1$=—($CH_2$)$_x$—C(O)—N$R_6R_7$, $R_2$=phenyloxypropyl, $R_3$=nitro, $R_6$=benzyl, $R_7$=carbamoylmethyl, n=1, x=1).

Example 91

N-benzyl-N-carbamoylmethyl-2-[7-benzoyl-3-(3-phenyloxypropyl)-2-oxobenzimidazolyl]ethanamide ($R_1$=—($CH_2$)$_x$—C(O)—N$R_6R_7$, $R_2$=phenyloxypropyl, $R_3$=benzoyl, $R_6$=benzyl, $R_7$=carbamoylmethyl, n=1, x=1).

Example 92

N-benzyl-N-carbamoylmethyl-2-[3-(3-phenyloxypropyl)-6-methoxycarbonyl-2-oxobenzimidazolyl]ethanamide ($R_1$=—($CH_2$)$_x$—C(O)—N$R_6R_7$, $R_2$=phenyloxypropyl, $R_3$=methoxycarbonyl, $R_6$=benzyl, $R_7$=carbamoylmethyl, n=1, x=1).

Example 93

N-benzyl-N-carbamoylmethyl-2-[3-(3-phenyloxypropyl)-2-oxo-5-trifluoromethylbenzimidazolyl]ethanamide ($R_1$=—($CH_2$)$_x$—C(O)—N$R_6R_7$, $R_2$=phenyloxypropyl, $R_3$=trifluoromethyl, $R_6$ benzyl, $R_7$=carbamoylmethyl, n=1, x=1).

Example 94

N-cyclohexylmethyl-N-carbamoylmethyl-2-[5,6-dimethyl-3-(3-phenyloxypropyl)-2-oxobenzimidazolyl]ethanamide ($R_1$=—($CH_2$)$_x$—C(O)—N$R_6R_7$, $R_2$=phenyloxypropyl, $R_3$=methyl, $R_6$=cyclohexylmethyl, $R_7$=carbamoylmethyl, n=2, x=1).

Example 95

N-(2-tetrahydrofuranylmethyl)-N-carbamoylmethyl-2-[7-benzoyl-3-(2,3,4,5,6-pentafluorobenzyl)-2-oxobenzimidazolyl]ethanamide ($R_1$=—($CH_2$)$_x$—C(O)—N$R_6R_7$, $R_2$=2,3,4,5,6-pentafluorobenzyl, $R_3$=benzoyl, $R_6$=2-tetrahydrofuranylmethyl, $R_7$=carbamoylmethyl, n=1, x=1).

Example 96

N-tetrahydrofuranylmethyl-N-carbamoylmethyl-2-[2-oxo-3-(2,3,4,5,6-pentafluoro-benzyl)-5-trifluoromethylbenzimidazolyl]ethanamide ($R_1$=—($CH_2$)$_x$—C(O)—N$R_6R_7$, $R_2$=2,3,4,5,6-pentafluorobenzyl, $R_3$=trifluoromethyl, $R_6$=2-tetrahydrofuranylmethyl, $R_7$=carbamoylmethyl, n=1, x=1).

Example 97

N-(3,5-Dimethoxybenzyl)-N-carbamoylmethyl-2-[2-oxo-3-(3-methoxybenzyl)-5-nitrobenzimidazolyl]ethanamide ($R_1$=—(CH$_2$)$_x$—C(O)—NR$_6$R$_7$, $R_2$=3-Methoxybenzyl, $R_3$=Nitro, $R_4$=3,5-dimethoxybenzyl, $R_7$=carbamoylmethyl, n=1, x=1).

Example 98

[N-carbamoylmethyl-N-[4'-(N'-ethoxycarbonyl-piperidinyl)]-2-[5,6-dimethyl-2-oxo-3-(3-phenyloxypropyl)benzimidazolyl]ethanamide ($R_1$=—(CH$_2$)$_x$—C(O)—NR$_6$R$_7$, $R_2$=3-phenyloxypropyl, $R_3$=methyl, $R_6$=N-ethoxy-carbonyl-piperidin-4-yl, $R_7$=carbamoylmethyl, n=2, x=1).

Example 99

[N-carbamoylmethyl-N-[4'-(N'-ethoxycarbonyl-piperidinyl)]-2-[7-benzoyl-2-oxo-3-(3-phenyloxyproply)benzimidazolyl]ethanamide ($R_1$=—(CH$_2$)$_x$—C(O)—NR$_6$R$_7$, $R_2$=3-phenyloxypropyl, $R_3$=benzoyl, $R_6$=N-ethoxy-carbonyl-piperidin-4-yl, $R_7$=carbamoylmethyl, n=1, x=1).

Example 100

[N-carbamoylmethyl-N-[4'-(N'-ethoxycarbonyl-piperidinyl)]-2-[6-methoxycarbonyl-2-oxo-3-(3-phenyloxypropyl)benzimidazolyl]ethanamide ($R_1$=—(CH$_2$)$_x$—C(O)—NR$_6$R$_7$, $R_2$=3-phenyloxypropyl, $R_3$=methoxycarbonyl, $R_6$=N-ethoxy-carbonyl-piperidin-4-yl, $R_7$=carbamoylmethyl, n=1, x=1).

Example 101

[N-carbamoylmethyl-N-[4'-(N'-ethoxycarbonyl-piperidinyl)]-2-[2-oxo-3-(3-phenyloxypropyl)-5-trifluoromethylbenzimidazolyl]ethanamide ($R_1$=—(CH$_2$)$_x$—C(O)—NR$_4$R$_7$, $R_2$=3-phenyloxypropyl, $R_3$=trifluoromethyl, $R_6$=N-ethoxy-carbonyl-piperidin-4-yl, $R_7$=carbamoylmethyl, n=1, x=1).

Example 102

[N-carbamoylmethyl-N-[4'-(N'-ethoxycarbonyl-piperidinyl)]-2-(5-methyl-2-oxo-3-(3-phenyloxypropyl)benzimidazolyl)acetylamino]-ethanamide ($R_1$=—(CH$_2$)$_x$—C(O)—NRR$_7$, $R_2$=3-phenyloxypropyl, $R_3$=methyl, $R_6$=N-ethoxy-carbonyl-piperidin-4-yl, $R_7$=carbamoylmethyl, n=1, x=1).

Example 103

N-(2-methylpropyl)-N-carbamoylmethyl-2-[5,6-Dimethyl-2-oxo-3-(3-phenyloxypropyl)benzimidazolyl]-ethanamide ($R_1$=—(CH$_2$)$_x$—C(O)—NR$_6$R$_7$, $R_2$=3-phenyloxypropyl, $R_3$=methyl, $R_6$=2-methylpropyl, $R_7$=carbamoylmethyl, n=2, x=1).

Example 104

N-(2-methylpropyl)-N-carbamoylmethyl-2-[3-benzoyloxyethyl-2-oxo-6-methoxycarbonylbenzimidazolyl]ethanamide ($R_1$=—(CH$_2$)$_x$—C(O)—NR$_6$R$_7$, $R_2$=3-phenyloxypropyl, $R_3$=methoxycarbonyl, $R_6$=2-methylpropyl, $R_7$=carbamoylmethyl, n=1, x=1).

Example 105

N-(4-diethylaminophenyl)-N-carbamoylmethyl-2-[5-nitro-2-oxo-3-(3-phenyloxypropyl)benzimidazolyl]-ethanamide ($R_1$=—(CH$_2$)$_x$—C(O)—NR$_6$R$_7$, $R_2$=3-phenyloxypropyl, $R_3$=nitro, $R_6$=2-methylpropyl, $R_7$=carbamoylmethyl, n=1, x=1).

Example 106

N-(4-diethylaminophenyl)-N-carbamoylmethyl-2-[6-methoxycarbonyl-2-oxo-3-(3-phenyloxypropyl)benzimidazolyl]-ethanamide ($R_1$=—(CH$_2$)$_x$—C(O)—NR$_6$R$_7$, $R_2$=3-phenyloxypropyl, $R_3$=methoxycarbonyl, $R_6$=4-diethylaminophenyl, $R_7$=carbamoylmethyl, n=1, x=1).

Example 107

N-(4-diethylaminophenyl)-N-carbamoylmethyl-2-[2-oxo-3-(3-phenyloxypropyl)-5-trifluoromethylbenzimidazolyl]-ethanamide ($R_1$=—(CH$_2$)$_x$—C(O)—NR$_6$R$_7$, $R_2$=3-phenyloxypropyl, $R_3$=trifluoromethyl, $R_6$=4-diethylaminophenyl, $R_7$=carbamoylmethyl, n=1, x=1).

Example 108

N-(4-diethylaminophenyl)-N-carbamoylmethyl-2-[5-Methyl-2-oxo-3-(3-phenyloxypropyl)benzimidazolyl]-ethanamide ($R_1$=—(CH$_2$)$_x$—C(O)—NR$_6$R$_7$, $R_2$=3-phenyloxypropyl, $R_3$=methyl, $R_6$=4-diethylaminophenyl, $R_7$=carbamoylmethyl, n=1, x=1).

Example 109

N-(2-tetrahydrofuranylmethyl)-N-carbamoylmethyl-2-[5,6-dimethyl-2-oxo-3-(3-phenyloxypropyl)benzimidazolyl]-ethanamide ($R_1$=—(CH$_2$)$_x$—C(O)—NR$_6$R$_7$, $R_2$=3-phenyloxypropyl, $R_3$=methyl, $R_6$=2-tetrahydrofuranylmethyl, $R_7$=carbamoylmethyl, n=2, x=1).

Example 110

N-(2-tetrahydrofuranylmethyl)-N-carbamoylmethyl-2-[5-nitro-2-oxo-3-(3-phenyloxypropyl)benzimidazolyl]-ethanamide ($R_1$=—(CH$_2$)$_x$—C(O)—NR$_6$R$_7$, $R_2$=3-phenyloxypropyl, $R_3$=nitro, $R_6$=2-tetrahydrofuranylmethyl, $R_7$=carbamoylmethyl, n=1, x=1).

Example 111

N-(2-tetrahydrofuranylmethyl)-N-carbamoylmethyl-2-[6-methoxycarbonyl-2-oxo-3-(3-phenyloxypropyl) benzimidazolyl]-ethanamide ($R_1$=—$(CH_2)_x$—C(O)—$NR_6R_7$, $R_2$=3-phenyloxypropyl, $R_3$=methoxycarbonyl, $R_6$=2-tetrahydrofuranylmethyl, $R_7$=carbamoylmethyl, n=1, x=1).

Example 112

N-(3,5-Dimethoxybenzyl)-N-carbamoylmethyl-2-[7-benzoyl-3-(3-methoxybenzyl)-2-oxobenzimidazolyl]-ethanamide ($R_1$=—$(CH_2)_x$—C(O)—$NR_6R_7$, $R_2$=3-methoxybenzyl, $R_3$=benzoyl, $R_6$=3,5-dimethoxybenzyl, $R_7$=carbamoylmethyl, n=1, x=1).

Example 113

N-(3,5-Dimethoxybenzyl)-N-carbamoylmethyl-2-[6-methoxycarbonyl-3-(3-methoxybenzyl)-2-oxobenzimidazolyl]-ethanamide ($R_1$=—$(CH_2)_x$—C(O)—$NR_6R_7$, $R_2$=3-methoxybenzyl, $R_3$=methoxycarbonyl, $R_6$=3,5dimethoxybenzyl, $R_7$=carbamoylmethyl, n=1, x=1).

Example 114

N-Benzyl-N-carbamoylmethyl-2-[5-methyl-3-(3,3-dimethyl-2-oxo-butyl)-2-oxobenzimidazolyl]-ethanamide ($R_1$=—$(CH_2)_x$—C(O)—$NR_6R_7$, $R_2$=3,3-dimethyl-2-oxo-butyl, $R_3$=methyl, $R_6$=benzyl, $R_7$=carbamoylmethyl, n=1, x=1).

Example 115

N-(3,5-Dimethoxybenzyl)-N-carbamoylmethyl-2-[6-fluoro-3-(3-methoxybenzyl)-2-oxobenzimidazolyl]-ethanamide ($R_1$=—$(CH_2)_x$—C(O)—$NR_6R_7$, $R_2$=3-methoxybenzyl, $R_3$=fluoro, $R_6$=3,5-dimethoxybenzyl, $R_7$=carbamoylmethyl, n=1, x=1).

Example 116

N-Cyclohexyl-N-carbamoylmethyl-2-[5,6-dimethyl-3-(3,3-dimethyl-2-oxo-butyl)-2-oxobenzimidazolyl]-ethanamide ($R_1$=—$(CH_2)_x$—C(O)—$NR_6R_7$, $R_2$=3,3-dimethyl-2-oxo-butyl, $R_3$=methyl, $R_6$=cyclohexyl, $R_7$=carbamoylmethyl, n=2, x=1).

Example 117

N-(4-diethylaminophenyl)-N-carbamoylmethyl-2-[3-(3,3-dimethyl-2-oxo-butyl)-5-nitro-2-oxobenzimidazolyl]-ethanamide ($R_1$=—$(CH_2)_x$—C(O)—$NR_6R_7$, $R_2$=3,3-dimethyl-2-oxo-butyl, $R_3$=nitro, $R_6$=4-diethylaminophenyl, $R_7$=carbamoylmethyl, n=1, x=1).

Example 118

[N-(3,5-Dimethoxybenzyl)-N-carbamoylmethyl]2-[4-benzoyl-3-(4'-methoxycarbonylbenzyl)-2-oxobenzimidazolylmethyl]ethanamide ($R_1$=—$(CH_2)_x$—C(O)—$NR_6R_7$, $R_2$=methoxycarbonylbenzyl, $R_3$=benzoyl, $R_6$=3,5-dimethoxybenzyl, $R_7$=carbamoylmethyl, n=1, x=1).

Example 119

[N-(3,5-Dimethoxybenzyl)-N-carbamoylmethyl]2 [6-methyl-3-(4'-methoxycarbonylbenzyl)-2-oxobenzimidazolyl]ethanamide ($R_1$=—$(CH_2)_x$—C(O)—$NR_6R_7$, $R_2$=methoxycarbonylbenzyl, $R_3$=methyl, $R_6$=3,5-dimethoxybenzyl, $R_7$=carbamoylmethyl, n=1, x=1).

Example 120

[N-(3,5-Dimethoxybenzyl)-N-carbamoylmethyl]-2-[6-nitro-2-oxobenzimidazolyl]ethanamide ($R_1$=—$(CH_2)_x$—C(O)—$NR_6R_7$, $R_2$=methoxycarbonylbenzyl, $R_3$=nitro, $R_6$=3,5-dimethoxybenzyl, $R_7$=carbamoylmethyl, n=1, x=1).

Example 121

N-(4-diethylaminophenyl)-N-carbamoylmethyl-2-[7-benzoyl-3-(3-methoxybenzyl)-2-oxobenzimidazolyl]-ethanamide ($R_1$=—$(CH_2)_x$—C(O)—$NR_6R_7$, $R_2$=3-methoxybenzyl, $R_3$=benzoyl, $R_6$=4-diethylaminophenyl, $R_7$=carbamoylmethyl, n=1, x=1).

Example 122

[N-Carbamoylmethyl-N-[4'-(N'-ethoxycarbonyl-piperdinyl)]-2-(7-benzoyl-2-oxo-3-(4-methoxycarbonylbenzyl)benzimidazolyl)ethanamide ($R_1$=—$(CH_2)_x$—C(O)—$NR_6R_7$, $R_2$=4-methoxycarbonylbenzyl, $R_3$=benzoyl, $R_6$=N-ethoxycarbonyl-piperidin-4-yl, $R_7$=carbamoylmethyl, n=1, x=1).

Example 123

[N-(2-methylpropyl)-N-carbamoylmethyl]-2-[6-nitro-3-(4'-(methoxycarbonylbenzyl)] oxobenzimidazolyl]ethanamide ($R_1$=—$(CH_2)_x$—C(O)—$NR_6R_7$, $R_2$=4-methoxycarbonylbenzyl, $R_3$=nitro, $R_6$=2-methylpropyl, $R_7$=carbamoylmethyl, n=1, x=1).

Example 124

N-benzyl-N-carbamoylmethyl-2-[3-(3-methoxybenzyl)-5-Nitro-2-oxobenzimidazolyl]-ethanamide ($R_1$=—$(CH_2)_x$—C(O)—$NR_6R_7$, $R_2$=3-methoxybenzyl, $R_3$=nitro, $R_6$=benzyl, $R_7$=carbamoylmethyl, n=1, x=1).

Example 125

[N-(4-diethylaminophenyl)-N-carbamoylmethyl]-2-[5,6-dimethyl-3-(4'-(methoxycarbonylbenzyl)-2-oxobenzimidazolyl]ethanamide ($R_1$=—($CH_2$)$_x$—C(O)—$NR_6R_7$, $R_2$=4-methoxycarbonylbenzyl, $R_3$=methyl, $R_6$=4-diethylaminophenyl, $R_7$=carbamoylmethyl, n=2, x=1).

Example 126

[N-(4-diethylaminophenyl)-N-carbamoylmethyl]-2-[6-nitro-3-(4'-(methoxycarbonylbenzyl)-2-oxobenzimidazolyl]ethanamide ($R_1$=—($CH_2$)$_x$—C(O)—$NR_6R_7$, $R_2$=4-methoxycarbonylbenzyl, $R_3$=nitro, $R_6$=4-diethylaminophenyl, $R_7$=carbamoylmethyl, n=1, x=1).

Example 127

[N-(4-diethylaminophenyl)-N-carbamoylmethyl]-2-[4-benzoyl-3-(4'-(methoxycarbonylbenzyl-2-oxobenzimidazolyl]ethanamide ($R_1$=—($CH_2$)$_x$—C(O)—$NR_6R_7$, $R_2$=4-methoxycarbonylbenzyl, $R_3$=benzoyl, $R_6$=4-diethylaminophenyl, $R_7$=carbamoylmethyl, n=1, x=1).

Example 128

[N-(4-diethylaminophenyl)-N-carbamoylmethyl]-2-[5-methoxycarbonyl-3-(4'-(methoxycarbonylbenzyl)-2-oxobenzimidazolyl]ethanamide ($R_1$=—($CH_2$)$_x$—C(O)—$NR_6R_7$, $R_2$=4-methoxycarbonylbenzyl, $R_3$=methoxycarbonyl, $R_6$=4-diethylaminophenyl, $R_7$=carbamoylmethyl, n=1, x=1).

Example 129

[N-(4-diethylaminophenyl)-N-carbamoylmethyl]-2-[2-oxo-3-(4'-(methoxycarbonylbenzyl)-6-trifluoromethylbenzimidazolyl]ethanamide ($R_1$=—($CH_2$)$_x$—C(O)—$NR_6R_7$, $R_2$=4-methoxycarbonylbenzyl, $R_3$=trifluoromethyl, $R_6$=4-diethylaminophenyl, $R_7$=carbamoylmethyl, n=1, x=1).

Example 130

[N-(4-diethylaminophenyl)-N-carbamoylmethyl] carbamoylmethyl-5-fluoro-3-(4'-(methoxycarbonylbenzyl)2-oxobenzimidazolylmethyl Ethanamide ($R_1$=—($CH_2$)$_x$—C(O)—$NR_6R_7$, $R_2$=4-methoxycarbonylbenzyl, $R_3$=fluoro, $R_6$=4-diethylaminophenyl, $R_7$=carbamoylmethyl, n=1, x=1).

Example 131

[N-(2-tetrahydrofuranylmethyl)-N-carbamoylmethyl]-2-[5,6-dimethyl-3-(4'-(methoxycarbonylbenzyl)-2-oxobenzimidazolyl]ethanamide ($R_1$=—($CH_2$)$_x$—C(O)—$NR_6R_7$, $R_2$=4-methoxycarbonylbenzyl, $R_3$ methyl, $R_6$=2-tetrahydrofuranylmethyl, $R_7$=carbamoylmethyl, n=2, x=1).

Example 132

[N-(2-tetrahydrofuranylmethyl)-N-carbamoylmethyl]-2-[5-methoxycarbonyl-3-(4'-(methoxycarbonylbenzyl)-2-oxobenzimidazolyl]ethanamide ($R_1$=—($CH_2$)$_x$—C(O)—$NR_{67}$, $R_2$=4-methoxycarbonylbenzyl, $R_3$=methoxycarbonyl, $R_6$=2-tetrahydrofuranylmethyl, $R_7$=carbamoylmethyl, n=1, x=1).

Example 133

[N-(2-tetrahydrofuranylmethyl)-N-carbamoylmethyl]—2[3-(4'-(methoxycarbonylbenzyl)-2-oxo-6-trifluoromethylbenzimidazolyl]ethanamide ($R_1$=—($CH_2$)$_x$—C(O)—$NR_6R_7$, $R_2$=4-methoxycarbonylbenzyl, $R_3$=trifluoromethyl, $R_6$=2-tetrahydrofuranylmethyl, $R_7$=carbamoylmethyl, n=1, x=1).

Example 134

[N-(3,5-Dimethoxybenzyl)-N-carbamoylmethyl]-2-[3-ethoxycarbonylmethyl-5,6-dimethyl-2-oxobenzimidazolyl]ethanamide ($R_1$=—($CH_2$)$_x$—C(O)—$NR_6R_7$, $R_2$=ethoxycarbonylmethyl, $R_3$=methyl, $R_6$=3,5-dimethoxybenzyl, $R_7$=carbamoylmethyl, n=2, x=1).

Example 135

[N-(3,5-Dimethoxybenzyl)-N-carbamoylmethyl]2-[3-ethoxycarbonylmethyl-6-nitro-2-oxobenzimidazolyl]ethanamide ($R_1$=—($CH_2$)$_x$—C(O)—$NR_6R_7$, $R_2$=ethoxycarbonylmethyl, $R_3$=nitro, $R_6$=3,5-dimethoxy-benzyl, $R_7$=carbamoylmethyl, n=1, x=1).

Example 136

[N-(3,5-Dimethoxybenzyl)-N-carbamoylmethyl]2-[3-ethoxycarbonylmethyl-7-benzoyl-2-oxobenzimidazolyl]acetate ($R_1$=—($CH_2$)$_x$—C(O)—$NR_6R_7$, $R_2$=ethoxycarbonylmethyl, $R_3$=benzoyl, $R_6$=3,5-dimethoxybenzyl, $R_7$=carbamoylmethyl, n=1, x=1).

Example 137

[N-(3,5-Dimethoxybenzyl)-N-carbamoylmethyl]2-[3-ethoxycarbonylmethyl-5-methoxycarbonyl-2-oxobenzimidazolyl]ethanamide ($R_1$=—($CH_2$)$_x$—C(O)—$NR_6R_7$, $R_2$=ethoxycarbonylmethyl, $R_3$=methoxycarbonyl, $R_6$=3,5-dimethoxy-benzyl, $R_7$=carbamoylmethyl, n=1, x=1).

Example 138

[N-(3,5-Dimethoxybenzyl)-N-carbamoylmethyl]-2-[2-oxo-3-ethoxycarbonylmethyl-6-trifluoromethylbenzimidazolyl]ethanamide ($R_1$=—($CH_2$)$_x$—C(O)—$NR_6R_7$, $R_2$=ethoxycarbonylmethyl, $R_3$=trifluoromethyl, $R_6$=3, 5-dimethoxybenzyl, $R_7$=carbamoylmethyl, n=1, x=1).

Example 139

[N-(3,5-Dimethoxybenzyl)-N-carbamoylmethyl]-2-[2-oxo-3-ethoxycarbonylmethyl-5-fluorobenzimidazolyl]ethanamide ($R_1$=—($CH_2$)$_x$—C(O)—$NR_6R_7$, $R_2$=ethoxycarbonylmethyl, $R_3$=fluoro, $R_6$=3,5-dimethoxybenzyl, $R_7$=carbamoylmethyl, n=1, x=1).

Example 140

[N-(2-tetrahydrofuranylmethyl)-N-carbamoylmethyl]-2-[2-oxo-3-ethoxycarbonylmethyl-5-fluorobenzimidazolyl]ethanamide ($R_1$=—($CH_2$)$_x$—C(O)—$NR_6R_7$, $R_2$=ethoxycarbonylmethyl, $R_3$=fluoro, $R_6$=2-tetrahydro-furanylmethyl, $R_7$=carbamoylmethyl, n=1, x=1).

Example 141

[N-(3-Bromobenzyl)-N-carbamoylmethyl]-2-[3-ethoxycarbonylmethyl-5-fluoro-2-oxobenzimidazolyl]ethanamide ($R_1$=—($CH_2$)$_x$—C(O)—$NR_6R_7$, $R_2$=ethoxycarbonylmethyl, $R_3$=fluoro, $R_6$=3-bromobenzyl, $R_7$=carbamoylmethyl, n=1, x=1).

Example 142

[N-(3-Bromobenzyl)-N-carbamoylmethyl]2-[3-ethoxycarbonylmethyl-6-methyl-2-oxobenzimidazolyl]ethanamide ($R_1$=—($CH_2$)$_x$—C(O)—$NR_6R_7$, $R_2$=ethoxycarbonylmethyl, $R_3$=methyl, $R_6$=3-bromobenzyl, $R_7$=carbamoylmethyl, n=1, x=1).

Example 143

N-Benzyl-N-carbamoylmethyl-2-[7-benzoyl-2-oxo-3-(3-methoxybenzylbenzimidazolyl]ethanamide ($R_1$=—($CH_2$)$_x$—C(O)—$NR_6R_7$, $R_2$=methoxybenzyl, $R_3$=benzoyl, $R_6$=benzyl, $R_7$=carbamoylmethyl, n=1, x=1).

Example 144

[N-Carbamoylmethyl-3-ethoxycarbonylethyl-2-[(5,6-dimethyl-3-ethoxycarbonylmethyl-2-oxobenzimidazolyl]ethanamide ($R_1$=—($CH_2$)$_x$—C(O)—$NR_6R_7$, $R_2$=ethoxycarbonylmethyl, $R_3$=methyl, $R_6$=ethoxycarbonylethyl, $R_7$=carbamoylmethyl, n=2, x=1).

Example 145

[N-Carbamoylmethyl-N-[N'-ethoxycarbonylpiperdinyl)]-2-[5,6-dimethyl-3-methoxybenzyl-2-oxobenzimidazolyl]ethanamide ($R_1$=—($CH_2$)$_x$—C(O)—$NR_6R_7$, $R_2$=methoxybenzyl, $R_3$=methyl, $R_6$=N-ethoxy-carbonylpiperidin-4-yl, $R_7$=carbamoylmethyl, n=2, x=1).

Example 146

[N-Carbamoylmethyl-N-[4'-(N'-ethoxycarbonylphenyl)]-2-[3-ethoxycarbonylmethyl-6-fluoro-2-oxobenzimidazolyl]ethanamide ($R_1$=—($CH_2$)$_x$—C(O)—$NR_6R_7$, $R_2$=ethoxycarbonylmethyl, $R_3$=fluoro, $R_6$ ethoxycarbonylphenyl, $R_7$=carbamoylmethyl, n=1, x=1).

Example 147

[N-Carbamoylmethyl-N-(4'-ethoxycarbonylphenyl)-2-[3-ethyoxycarbonylmethyl-5-methyl-2-oxobenzimidazolyl]ethanamide ($R_1$=—($CH_2$)$_x$—C(O)—$NR_6R_7$, $R_2$=ethoxycarbonylmethyl, $R_3$=methyl, $R_6$=ethoxycarbonylphenyl, $R_7$=carbamoylmethyl, n=1, x=1).

Example 148

[N-Carbamoylmethyl-N-[4'(N'-ethoxycarbonylpiperidinyl)]-2-(3-ethoxycarbonylmethyl-6-methoxycarbonyl-2-oxobenzimidazolyl)ethanamide ($R_1$=—($CH_2$)$_x$—C(O)—$NR_6R_7$, $R_2$=ethoxycarbonylmethyl, $R_3$=methoxycarbonyl, $R_6$=N-ethoxy-carbonylpiperidin-4-yl, $R_7$=carbamoylmethyl, n=2, x=1).

Example 149

[N-(4-diethylaminophenyl)-N-carbamoylmethyl]-2-[4-benzoyl-3-ethoxycarbonylmethyl-2-oxobenzimidazolyl]ethanamide ($R_1$=—($CH_2$)$_x$—C(O)—$N_6R_7$, $R_2$=ethoxycarbonylmethyl, $R_3$=benzoyl, $R_6$=4-diethylaminophenyl, $R_7$=carbamoylmethyl, n=1, x=1).

Example 150

[N-(4-diethylaminophenyl)-N-carbamoylmethyl]-2-[3ethyoxycarbonylmethyl-5-methoxycarbonyl-2-oxobenzimidazolyl]ethanamide ($R_1$=—($CH_2$)$_x$—C(O)—$NR_6R_7$, $R_2$=ethoxycarbonylmethyl, $R_3$=methoxycarbonyl, $R_6$=4-diethylaminophenyl, $R_7$=carbamoylmethyl, n=1, x=1).

Example 151

[N-(4-diethylaminophenyl)-N-carbamoylmethyl]-2-[3ethyoxycarbonylmethyl-5-fluoro-2-oxobenzimidazolyl]ethanamide ($R_1$=—($CH_2$)$_x$—C(O)—$NR_6R_7$, $R_2$=ethoxycarbonylmethyl, $R_3$=fluoro, $R_6$=4-diethylaminophenyl, $R_7$=carbamoylmethyl, n=1, x=1).

Example 152

[N-(4-diethylaminophenyl)-N-carbamoylmethyl]-2-[3-ethoxycarbonylmethyl-6-methyl-2-oxobenzimidazolyl]ethanamide ($R_1$=—($CH_2$)$_x$—C(O)—$NR(R_7$, $R_2$=ethoxycarbonylmethyl, $R_3$=methyl, $R_6$=4-diethylaminophenyl, $R_7$=carbamoylmethyl, n=1, x=1).

Example 153

N-(2-tetrahydrofuranylmethyl)-N-carbamoylmethyl-2-[2-oxo-4-(2-propenyloxy)-3-(2-propenylbenzimidazolyl]ethanamide ($R_1$=—$(CH_2)_x$—C(O)—$NR_6R_7$, $R_2$=2-propenyl, $R_3$=2-propenyloxy, $R_6$=2-tetrahydrofuranylmethyl, $R_7$=carbamoylmethyl, n=1, x=1).

Example 154

N-(3,5-Dimethoxybenzyl)-N-carbamoylmethyl-2-[4-ethoxy-3-ethyl-2-oxobenzimidazolyl]ethanamide ($R_1$=—$(CH_2)_x$—C(O)—$NR_6R_7$, $R_2$=ethyl, $R_3$=ethoxy, $R_6$=3,5-dimethoxybenzyl, $R_7$=carbamoylmethyl, n=1, x=1).

Example 155

[N-carbamoylmethyl-N-(4'ethoxycarbonylphenyl)-2-(4-ethoxy-3-ethyl-2-oxobenzimidazolyl]ethanamide ($R_1$=—$(CH_2)_x$—C(O)—$NR_6R_7$, $R_2$=ethyl, $R_3$=ethoxy, $R_6$=4-ethoxycarbonylphenyl, $R_7$=carbamoylmethyl, n=1, x=1).

Example 156

N-(4-diethylaminophenyl)-N-carbamoylmethyl-2-[4-ethoxy-3-ethyl-2-oxobenzimidazolyl]ethanamide ($R_1$=—$(CH_2)_x$—C(O)—$NR_6R_7$, $R_2$=ethyl, $R_3$=ethoxy, $R_6$=4-diethylaminophenyl, $R_7$=carbamoylmethyl, n=1, x=1).

Example 157

N-(2-tetrahydrofuranylmethyl)-N-carbamoylmethyl-2-[4-ethoxy-3-ethyl-2-oxobenzimidazolyl]ethanamide ($R_1$=—$(CH_2)x$—C(O)—$NR_6R_7$, $R_2$=ethyl, $R_3$=ethoxy, $R_6$=2-tetrahydrofuranylmethyl, $R_7$=carbamoylmethyl, n=1, x=1).

The compounds of this invention can be formulated with pharmaceutically acceptable carriers into unit dosage forms in a conventional manner so that the patient in need of therapy for precancerous lesions can periodically (e.g., once or more per day) take a compound according to the methods of this invention. The exact initial dose of the compounds of this invention can be determined with reasonable experimentation. For compounds of this invention, a dosage of from about 0.1 to 400 mg of such compounds for intravenous administration to achieve a systemic circulatory therapeutic concentration.

It will be understood that various changes and modifications can be made in the details of procedure, formulation and use without departing from the spirit of the invention, especially as defined in the following claims.

We claim:

1. A method of treating a mammal having precancerous lesions comprising administering a pharmacologically effective amount of a compound of formula I

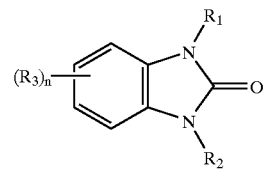

wherein $R_1$ is selected from a group consisting of lower alkyl, —$(CR_6R_7)$—$(CH_2)_x$—C(O)—$OR_4$, —$(CH_2)_x$—C(O)—$NHR_5$, or —$(CH_2)_x$—C(O)—$NR_6R_7$;

$R_2$ is selected from a group consisting of lower alkyl, alkenyl, —$(CH_2)_m$—$R_8$, substituted or unsubstituted aryl wherein said aryl group is selected from the group consisting of phenyl, benzyl, pyridyl, pyrimidyl, pyrazinyl, piperidyl, imidazolyl, indolyl, triazinyl, tetrazolyl, thiophenyl, furanyl, thiazolyl, pyrazolyl, and pyrrolyl, and wherein said substituents are one to five selected from the group consisting of halogen, lower alkyl, lower alkoxy, amino, nitro, and alkoxycarbonyl;

$R_3$ is selected from a group consisting of halogen, lower alkoxy, lower alkyl, benzoyl, nitro, haloalkyl, alkoxycarbonyl, lower alkenoxy, and aryloxy, wherein said aryl group is selected from a group consisting of phenyl and benzyl;

$R_4$ is hydrogen or lower alkyl;

$R_5$ is selected from a group consisting of hydrogen, lower alkyl, benzyl, pyridyl, pyrimidinyl, pyrazinyl, imidazolyl, indolyl, triazinyl, tetrazolyl, thiophenyl, furanyl, thiazolyl, pyrazolyl, and pyrrolyl;

$R_6$ and $R_7$ are independently selected from a group consisting of hydrogen, lower alkyl, tetrahydrofuranyl, tetrahydrofuranyl methyl, —$(CH_2)_x$—C(O)—$NH_2$, —$(CH_2)_x$—C(O)—$OR_4$, lower alkoxy, cyclohexylmethyl, substituted or unsubstituted phenyl, piperidyl, and benzyl, wherein said substituents are one to three selected from the group consisting of halogen, lower alkyl, lower alkoxy, lower alkoxycarbonyl, and diethylamine;

$R_8$ is selected from a group consisting of CN, alkylcarbonyloxy, lower alkylcarbonyl, and arylcarbonyloxy, wherein said aryl is one from a group consisting of phenyl and benzyl;

x is 0, 1 or 2;

m is 0, 1,2 or 3; and n is 0, 1, or 2.

2. The method of claim 1 wherein $R_1$ is selected from a group consisting of lower alkyl, —$(CH_2)_x$—C(O)—$NHR_5$, or —$(CH_2)_x$—C(O)—$NR_6R_7$;

$R_2$ is selected from a group consisting of substituted or unsubstituted aryl wherein said aryl group is selected from the group consisting of phenyl, benzyl, pyridyl, pyrimidyl, triazinyl, tetrazolyl, thiophenyl, furanyl, thiazolyl, pyrazolyl, and pyrrolyl, and wherein said substituents are one to three selected from the group consisting of halogen, lower alkoxy, amino, nitro, and alkoxycarbonyl;

$R_3$ is selected from a group consisting of halogen, lower alkoxy, lower alkyl, benzoyl, nitro, haloalkyl, alkoxycarbonyl, and aryloxy, wherein said aryl group is selected from a group consisting of phenyl and benzyl;

$R_5$ is selected from a group consisting of benzyl, pyridyl, pyrimidinyl, triazinyl, tetrazolyl, thiophenyl, furanyl, pyrazolyl, and pyrrolyl;

$R_6$ and $R_7$ are independently selected from a group consisting —$(CH_2)_x$—$C(O)$—$NH_2$, cyclohexylmethyl, substituted phenyl and benzyl, wherein said substituents are one or two selected from the group consisting of halogen, lower alkoxy, lower alkoxycarbonyl, and diethylamine;

$R_8$ is selected from a group consisting of lower alkylcarbonyl, and arylcarbonyloxy, wherein said aryl is benzyl;

x is 0, 1 or 2;

m is 0, 1, or 2; and n is 0, 1, or 2.

3. The method of claim 1 wherein $R_1$ is selected from a group consisting of —$(CH_2)_x$—$C(O)$—$NHR_5$, or —$(CH_2)_x$—$C(O)$—$NR_6R_7$;

$R_2$ is selected from a group consisting of substituted aryl wherein said aryl group is selected from the group consisting of phenyl, benzyl, pyridyl, pyrimidyl, and triazinyl, and wherein said substituents are two or three selected from the group consisting of halogen, lower alkoxy, amino, nitro, and alkoxycarbonyl;

$R_3$ is selected from a group consisting of halogen, lower alkoxy, benzoyl, haloalkyl, and alkoxycarbonyl, wherein said aryl group is selected from a group consisting of phenyl and benzyl;

$R_4$ is lower alkyl;

$R_5$ is selected from a group consisting of benzyl, pyridyl, pyrimidinyl, and triazinyl, $R_6$ and $R_7$ are independently selected from a group consisting —$(CH_2)_x$—$C(O)$—$NH_2$, substituted phenyl and benzyl, wherein said substituents are two selected from the group consisting of lower alkoxy, and diethylamine;

$R_8$ is arylcarbonyloxy, wherein said aryl is benzyl;

x is 0 or 1;

m is 0 or 1; and n is 0 or 1.

4. A method for inhibiting the growth of neoplastic cells comprising exposing the cells to a growth inhibiting effective amount of a compound of Formula I

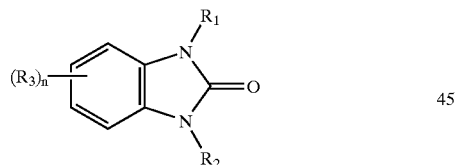

wherein $R_1$ is selected from a group consisting of lower alkyl, —$(CR_6R_7)$—$(CH_2)_x$—$C(O)$—$OR_4$, —$(CH_2)_x$—$C(O)$—$NHR_5$, or —$(CH_2)_x$—$C(O)$—$NR_6R_7$;

$R_2$ is selected from a group consisting of lower alkyl, alkenyl, —$(CH_2)_m$—$R_8$, substituted or unsubstituted aryl wherein said aryl group is selected from the group consisting of phenyl, benzyl, pyridyl, pyrimidyl, pyrazinyl, piperidyl, imidazolyl, indolyl, triazinyl, tetrazolyl, thiophenyl, furanyl, thiazolyl, pyrazolyl, and pyrrolyl, and wherein said substituents are one to five selected from the group consisting of halogen, lower alkyl, lower alkoxy, amino, nitro, and alkoxycarbonyl;

$R_3$ is selected from a group consisting of halogen, lower alkoxy, lower alkyl, benzoyl, nitro, haloalkyl, alkoxycarbonyl, lower alkenoxy, and aryloxy, wherein said aryl group is selected from a group consisting of phenyl and benzyl;

$R_4$ is hydrogen or lower alkyl;

$R_5$ is selected from a group consisting of hydrogen, lower alkyl, benzyl, pyridyl, pyrimidinyl, pyrazinyl, imidazolyl, indolyl, triazinyl, tetrazolyl, thiophenyl, furanyl, thiazolyl, pyrazolyl, and pyrrolyl;

$R_6$ and $R_7$ are independently selected from a group consisting of hydrogen, lower alkyl, tetrahydrofuranyl, tetrahydrofuranyl methyl, —$(CH_2)_x$—$C(O)$—$NH_2$, —$(CH_2)_x$—$C(O)$—$OR_4$, lower alkoxy, cyclohexylmethyl, substituted or unsubstituted phenyl, piperidyl, and benzyl, wherein said substituents are one to three selected from the group consisting of halogen, lower alkyl, lower alkoxy, lower alkoxycarbonyl, and diethylamine;

$R_8$ is selected from a group consisting of CN, alkylcarbonyloxy, lower alkylcarbonyl, and arylcarbonyloxy, wherein said aryl is one from a group consisting of phenyl and benzyl;

x is 0, 1 or 2;

m is 0, 1, 2 or 3; and n is 0, 1, or 2.

5. The method of claim 4 wherein $R_1$ is selected from a group consisting of lower alkyl, —$(CH_2)_x$—$C(O)$—$NHR_5$, or —$(CH_2)_x$—$C(O)$—$NR_6R_7$;

$R_2$ is selected from a group consisting of substituted or unsubstituted aryl wherein said aryl group is selected from the group consisting of phenyl, benzyl, pyridyl, pyrimidyl, triazinyl, tetrazolyl, thiophenyl, furanyl, thiazolyl, pyrazolyl, and pyrrolyl, and wherein said substituents are one to three selected from the group consisting of halogen, lower alkoxy, amino, nitro, and alkoxycarbonyl;

$R_3$ is selected from a group consisting of halogen, lower alkoxy, lower alkyl, benzoyl, nitro, haloalkyl, alkoxycarbonyl, and aryloxy, wherein said aryl group is selected from a group consisting of phenyl and benzyl;

$R_5$ is selected from a group consisting of benzyl, pyridyl, pyrimidinyl, triazinyl, tetrazolyl, thiophenyl, furanyl, pyrazolyl, and pyrrolyl;

$R_6$ and $R_7$ are independently selected from a group consisting —$(CH_2)_x$—$C(O)$—$NH_2$, cyclohexylmethyl, substituted phenyl and benzyl, wherein said substituents are one or two selected from the group consisting of halogen, lower alkoxy, lower alkoxycarbonyl, and diethylamine;

$R_8$ is selected from a group consisting of lower alkylcarbonyl, and arylcarbonyloxy, wherein said aryl is benzyl;

x is 0, 1 or 2;

m is 0, 1, or 2; and n is 0, 1, or 2.

6. A method for regulating apoptosis in human cells comprising exposing said cells to an effective amount of a compound of the formula:

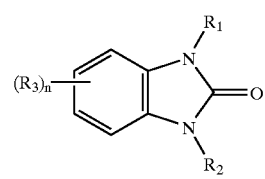

wherein
- $R_1$ is selected from a group consisting of lower alkyl, $-(CR_6R_7)-(CH_2)_x-C(O)-OR_4$, $-(CH_2)_x-C(O)-NHR_5$, or $-(CH_2)_x-C(O)-NR_6R_7$;
- $R_2$ is selected from a group consisting of lower alkyl, alkenyl, $(CH_2)_m-R_8$, substituted or unsubstituted aryl wherein said aryl group is selected from the group consisting of phenyl, benzyl, pyridyl, pyrimidyl, pyrazinyl, piperidyl, imidazolyl, indolyl, triazinyl, tetrazolyl, thiophenyl, furanyl, thiazolyl, pyrazolyl, and pyrrolyl, and wherein said substituents are one to five selected from the group consisting of halogen, lower alkyl, lower alkoxy, amino, nitro, and alkoxycarbonyl;
- $R_3$ is selected from a group consisting of halogen, lower alkoxy, lower alkyl, benzoyl, nitro, haloalkyl, alkoxycarbonyl, lower alkenoxy, and aryloxy, wherein said aryl group is selected from a group consisting of phenyl and benzyl;
- $R_4$ is hydrogen or lower alkyl;
- $R_5$ is selected from a group consisting of hydrogen, lower alkyl, benzyl, pyridyl, pyrimidinyl, pyrazinyl, imidazolyl, indolyl, triazinyl, tetrazolyl, thiophenyl, furanyl, thiazolyl, pyrazolyl, and pyrrolyl;
- $R_6$ and $R_7$ are independently selected from a group consisting of hydrogen, lower alkyl, tetrahydrofuranyl, tetrahydrofuranyl methyl, $-(CH_2)_x-C(O)-NH_2$, $-(CH_2)_x-C(O)-OR_4$, lower alkoxy, cyclohexylmethyl, substituted or unsubstituted phenyl, piperidyl, and benzyl, wherein said substituents are one to three selected from the group consisting of halogen, lower alkyl, lower alkoxy, lower alkoxycarbonyl, and diethylamine;
- $R_8$ is selected from a group consisting of CN, alkylcarbonyloxy, lower alkylcarbonyl, and arylcarbonyloxy, wherein said aryl is one from a group consisting of phenyl and benzyl;
- x is 0, 1 or 2;
- m is 0, 1, 2 or 3; and
- n is 0, 1, or 2.

7. The method of claim 6 wherein
- $R_1$ is selected from a group consisting of lower alkyl, $-(CH_2)_x-C(O)-NHR_5$, or $-(CH_2)_x-C(O)-NR_6R_7$;
- $R_2$ is selected from a group consisting of substituted or unsubstituted aryl wherein said aryl group is selected from the group consisting of phenyl, benzyl, pyridyl, pyrimidyl, triazinyl, tetrazolyl, thiophenyl, furanyl, thiazolyl, pyrazolyl, and pyrrolyl, and wherein said substituents are one to three selected from the group consisting of halogen, lower alkoxy, amino, nitro, and alkoxycarbonyl;
- $R_3$ is selected from a group consisting of halogen, lower alkoxy, lower alkyl, benzoyl, nitro, haloalkyl, alkoxycarbonyl, and aryloxy, wherein said aryl group is selected from a group consisting of phenyl and benzyl;
- $R_5$ is selected from a group consisting of benzyl, pyridyl, pyrimidinyl, triazinyl, tetrazolyl, thiophenyl, furanyl, pyrazolyl, and pyrrolyl;
- $R_6$ and $R_7$ are independently selected from a group consisting $-(CH_2)_x-C(O)-NH_2$, cyclohexylmethyl, substituted phenyl and benzyl, wherein said substituents are one or two selected from the group consisting of halogen, lower alkoxy, lower alkoxycarbonyl, and diethylamine;
- $R_8$ is selected from a group consisting of lower alkylcarbonyl, and arylcarbonyloxy, wherein said aryl is benzyl;
- x is 0, 1 or 2;
- m is 0, 1, or 2; and
- n is 0, 1, or 2.

\* \* \* \* \*